(12) United States Patent
Otto et al.

(10) Patent No.: US 8,252,550 B2
(45) Date of Patent: Aug. 28, 2012

(54) **TARGETING POLY-γ-GLUTAMIC ACID TO TREAT *STAPHYLOCOCCUS EPIDERMIDIS* AND RELATED INFECTIONS**

(75) Inventors: Michael Otto, Hamilton, MT (US);
Stanislava Kocianova, Worcester, MA (US); Cuong Vuong, Worcester, MA (US); Jovanka Voyich, Belgrade, MT (US); Yufeng Yao, Baltimore, MD (US); Elizabeth Fischer, Hamilton, MT (US); Frank De Leo, Corvallis, MT (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/035,716

(22) Filed: Feb. 25, 2011

(65) Prior Publication Data

US 2011/0217312 A1      Sep. 8, 2011

Related U.S. Application Data

(62) Division of application No. 11/994,984, filed as application No. PCT/US2006/026900 on Jul. 10, 2006, now abandoned.

(60) Provisional application No. 60/697,646, filed on Jul. 8, 2005.

(51) Int. Cl.
*A61K 39/385* (2006.01)

(52) U.S. Cl. .......................................... 435/36; 435/71.2

(58) Field of Classification Search ........................ None
See application file for complete search history.

(56) References Cited

U.S. PATENT DOCUMENTS

| 6,194,388 | B1 | 2/2001 | Krieg et al. |
| 6,207,646 | B1 | 3/2001 | Krieg et al. |
| 6,214,806 | B1 | 4/2001 | Krieg et al. |
| 6,218,371 | B1 | 4/2001 | Krieg et al. |

(Continued)

FOREIGN PATENT DOCUMENTS

JP     2005 187427     7/2005

(Continued)

OTHER PUBLICATIONS

Jama, Mar. 23/30, 2005 vol. 293(12), p. 1440, Health Agencies Update, Staph Bacteria Target.*

(Continued)

*Primary Examiner* — Albert Navarro
*Assistant Examiner* — Ginny Allen Portner
(74) *Attorney, Agent, or Firm* — Klarquist Sparkman, LLP

(57) ABSTRACT

Immunogenic compositions and methods for eliciting an immune response against *S. epidermidis* and other related staphylococci are provided. The immunogenic compositions can include immunogenic conjugates of poly-γ-glutamic acid (such as γDLPGA) polypeptides of *S. epidermidis*, or related staphylococci that express a γPGA polypeptide. The γPGA conjugates elicit an effective immune response against *S. epidermidis*, or other staphylococci, in subjects to which the conjugates are administered. A method of treating an infection caused by a *Staphylococcus* organism that expresses cap genes is also disclosed. The method can include selecting a subject who is at risk of or has been diagnosed with the infection by the *Staphylococcus* organism which expresses γPGA from the cap genes. Further, the expression of a γPGA polypeptide by the organism can then be altered.

4 Claims, 5 Drawing Sheets

U.S. PATENT DOCUMENTS

| | | | |
|---|---|---|---|
| 6,239,116 | B1 | 5/2001 | Krieg et al. |
| 6,339,068 | B1 | 1/2002 | Krieg et al. |
| 6,406,705 | B1 | 6/2002 | Davis et al. |
| 6,429,199 | B1 | 8/2002 | Krieg et al. |
| 6,610,293 | B1* | 8/2003 | Fischer et al. ............ 424/133.1 |
| 6,939,543 | B2* | 9/2005 | Fischer et al. ............ 424/133.1 |
| 2006/0140971 | A1* | 6/2006 | Sung et al. ................. 424/190.1 |
| 2009/0203790 | A1* | 8/2009 | Yamamoto et al. ........... 514/561 |
| 2009/0280513 | A1* | 11/2009 | Kozel et al. ................. 435/7.94 |

FOREIGN PATENT DOCUMENTS

| | | |
|---|---|---|
| WO | WO 01/60412 | 8/2001 |
| WO | WO 2005/007804 | 1/2005 |
| WO | WO 2005/048918 | 6/2005 |

OTHER PUBLICATIONS

Ken Pekoc, NIH/National Institue of Allergy and Infectious Diseases, Substance protects resilient staph bacteria, public release date, Feb. 3, 2005, Back to EurekAlert, pp. 1-2.*

An, Yuehuei H et al, Journal of Microbiological Methods, vol. 30, pp. 141-152, 1997, Laboratory methods for studies of bacterial adhesion.*

Candela et al., "CapE, a 47-amino-acid peptide, is necessary for *Bacillus anthracis* polyglutamate capsule synthesis," *J. Bacteriol.*, 187(22):7765-7772, 2005.

Candela et al., "Poly-gamma-glutamate in bacteria," *Molecular Microbiology*, 60(5):1091-1098, 2006.

Ezzell et al., "Identification of *Bacillus anthracis* by using monoclonal antibody to cell wall galactose-N-acetylglucosamine polysaccharide," *J. Clin. Microbiol.*, 28(2):223-231, 1990.

Kocianova et al., "Key role of poly-gamma-DL-glutamic acid in immune evasion and virulence of *Staphylococcus epidermidis*," *J. Clin. Invest.*, 115(3):688-694, 2005.

Saruta et al., "Rapid identification and typing of *Staphylococcus aureus* by nested PCR amplified ribosomal DNA spacer region," *FEMS Microbiol. Lett.*, 146(2):271-278, 1997.

Schneerson et al., "Poly(gamma-D-glutamic acid) protein conjugates induce IgG antibodies in mice to the capsule of *Bacillus anthracis*: a potential addition to the anthrax vaccine," *Proc. Natl. Acad. Sci. USA*, 100(15):8945-8950, 2003.

Scorpio et al., "Poly-γ-Glutamate Capsule-Degrading Enzyme Treatement Enhances Phagocytosis and Killing of Encapsulated *Bacillus anthracis*," *Antimicrobial Agents and Chemotherapy*, 51:215-222, 2007.

Vuong and Otto, "*Staphylococcus epidermidis* infections," *Microbes Infect.*, 4(4):481-489, 2002.

Vuong et al., "Polysaccharide intercellular adhesin (PIA) protects *Staphylococcus epidermidis* against major components of the human innate immune system," *Cell. Microbiol.*, 6(3):269-275, 2004.

Zhang et al., "Genome-based analysis of virulence genes in a non-biofilm-forming *Staphylococcus epidermidis* strain (ATCC 12228)" *Mol. Microbiol.*, 49(6):1577-1593, 2003.

* cited by examiner

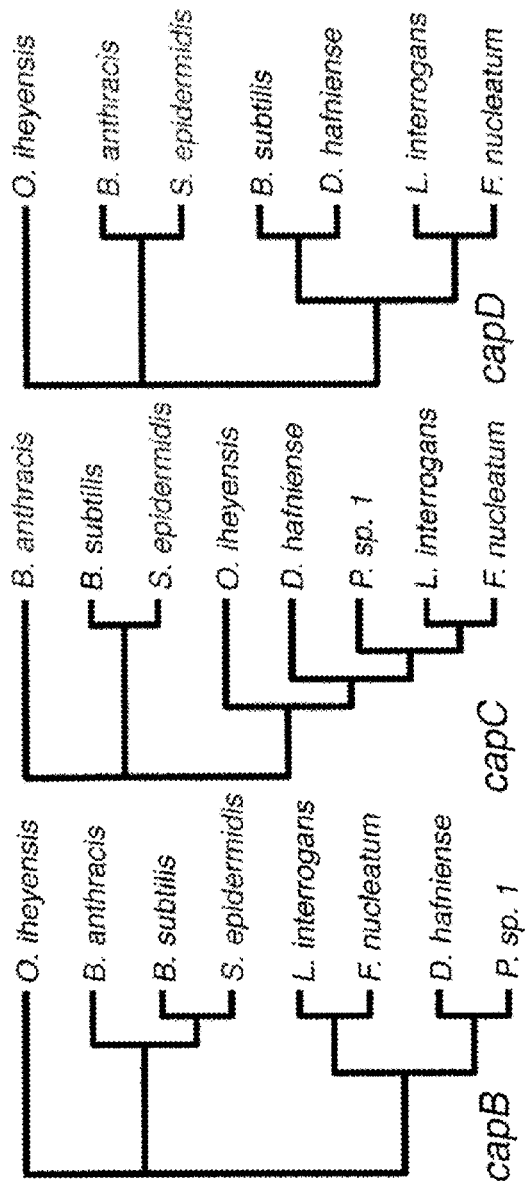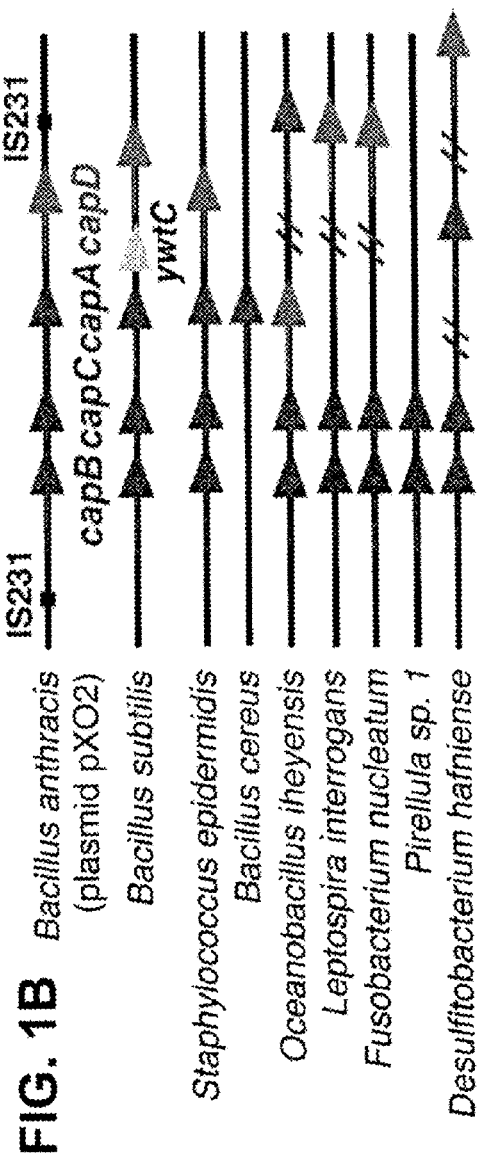
FIG. 1A
FIG. 1B

TARGETING POLY-γ-GLUTAMIC ACID TO TREAT *STAPHYLOCOCCUS EPIDERMIDIS* AND RELATED INFECTIONS

CROSS REFERENCE TO RELATED APPLICATIONS

This is a divisional application of U.S. application Ser. No. 11/994,984, filed Jan. 7, 2008 now abandoned, which is the §371 U.S. National Stage of International Application No. PCT/US2006/026900, filed Jul. 10, 2006, which was published in English under PCT Article 21(2), which in turn claims the benefit of U.S. Provisional Patent Application No. 60/697,646, filed Jul. 8, 2005. The entire disclosures of the prior applications are considered to be part of the disclosure of the accompanying application and are hereby incorporated by reference.

FIELD OF THE DISCLOSURE

This invention relates to the field of infectious disease, and the treatment of certain infections, such as *Staphylococcus epidermidis* infections, and to immunogenic compositions and methods for eliciting an immune response against *Staphylococcus epidermidis*.

BACKGROUND

Coagulase-negative staphylococci, with the leading species *Staphylococcus epidermidis* (*S. epidermidis*), have over the past decade become the most prevalent pathogens involved in hospital-acquired infections (Vuong, C., and Otto, M. *Microbes Infect.* 4: 481-489, 2002). For example, in the United States alone, *S. epidermidis* infections on in-dwelling medical devices cost the public health system approximately one billion dollars per year (Vuong, C., and Otto, M. *Microbes Infect.* 4: 481-489, 2002).

*S. epidermidis* is usually an innocuous commensal microorganism on human skin. This microorganism can cause severe infection after penetration of the epidermal protective barriers of the human body. To survive on the human skin and during infection of in-dwelling medical devices, *S. epidermidis* circumvents human innate host defenses (Hornef, M. W., Wick, M. J., Rhen, M., and Normark, S. *Nat. Immunol.* 3: 1033-1040, 2002). For example, *S. epidermidis* is frequently resistant to common antibiotics (Vuong, C., and Otto, M. *Microbes Infect.* 4:481-489, 2002). The formation of surface-attached cellular agglomerations known as biofilms is believed to contribute significantly to antibiotic resistance and protection of the organism from innate host defense (Costerton, J. W., Steward, P. S., and Greenberg, E. P. *Science*. 284: 1318-1322, 1999). Further, it has been suggested that resistance of *S. epidermidis* biofilms to some antibiotics is in part due to a status of generally reduced metabolism (Yao, Y., Sturdevant, D. E., and Otto, M. *J. Infect. Dis.* 191: 289-298, 2005). Thus, *S. epidermidis* is one of the difficult hard-to-treat infectious agents that can be transmitted nosocomially to patients in hospitals, especially such patients who have in-dwelling medical implants.

It would be advantageous to provide compositions and methods of treating staphylococcal infections, such as coagulase-negative staphylococcal infections, for example *S. epidermidis* infections.

SUMMARY

Certain staphylococci secrete poly-γ-glutamic acid (γPGA) that has now been found to facilitate growth and survival of these bacterial pathogens in hosts. γPGA efficiently shelters these pathogens from innate host immune defenses, such as antimicrobial peptides and neutrophil phagocytosis, and is important for microbial persistence during an infection, such as a device-related infection. The γPGA also protects the organism against other antimicrobial defenses, such as the high salt concentration that is found on the skin. The γPGA therefore presents an important new biological target for therapies aimed at treating diseases caused by staphylococci that secrete γPGA, such as coagulase-negative staphylococci, including *S. epidermidis*. In certain embodiments, the γPGA target is poly-γ-D-L-glutamic acid (γDLPGA), which is preferentially expressed by *S. epidermidis*.

An immunogenic conjugate is disclosed. In an aspect, the immunogenic conjugate includes a *Staphylococcus* capsular γPGA polypeptide and an adjuvant. For example, the conjugate may be linked to a carrier protein. The conjugate elicits an immune response in a subject. In one example, the conjugate is administered to treat, reduce, ameliorate or prevent a coagulase-negative *staphylococcus*-induced infection such as an *S. epidermidis* infection on an in-dwelling medical device.

A method is also disclosed for treating (including preventing) an infection caused by a *Staphylococcus* organism that secretes γPGA polypeptides, for example an organism that expresses cap genes. The method can include selecting a subject who is at risk of or has been diagnosed with the infection by the *Staphylococcus* organism which expresses γPGA and interfering with the microbial protective effect provided by the γPGA. In some examples, this interference takes the form of stimulating an immune response against the γPGA, administering antisera against it, or disrupting expression of the γPGA by the organism.

BRIEF DESCRIPTION OF THE FIGURES

FIG. 1A is a schematic representation of phylogenetic trees based on sequence comparisons of capB (amide ligase), capC (unknown function) and capD (depolymerase) genes.

FIG. 1B is a gene locus map of various cap genes and homologs in bacteria.

SEQUENCE LISTING

Figures 2A, 2B, 2C:
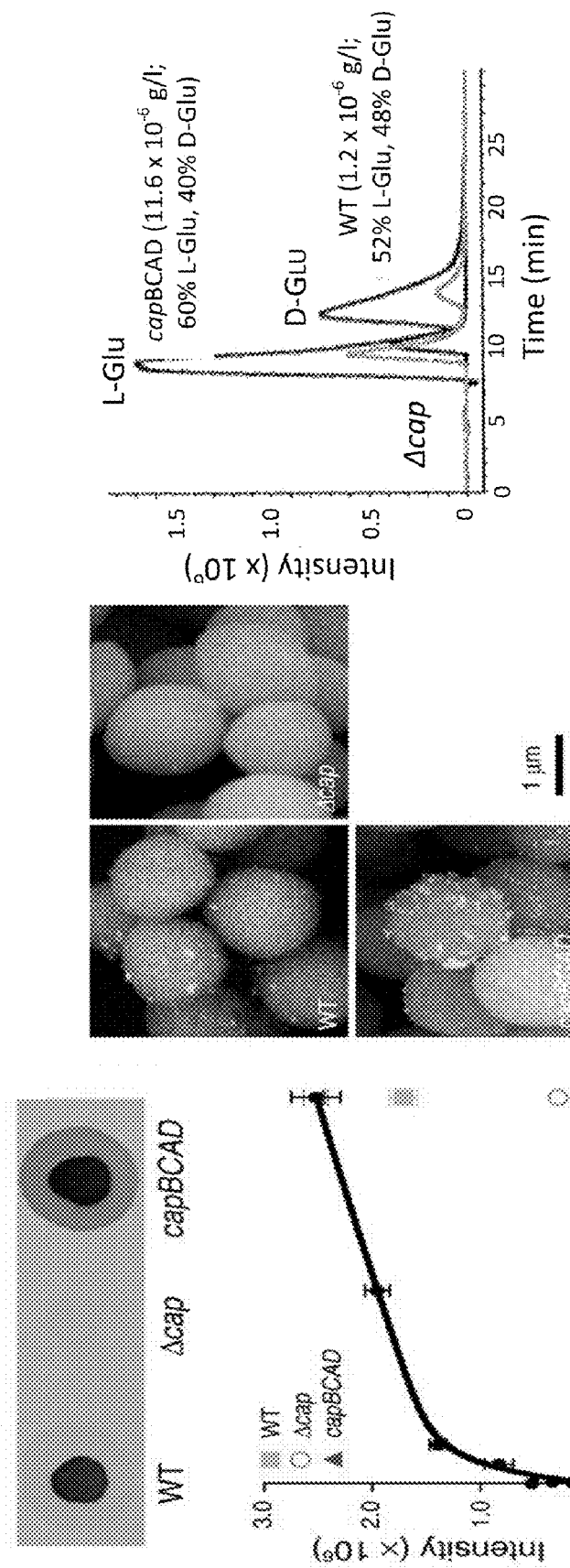
FIG. 2A shows a representative immuno-dot blot and a graph of the relative γPGA expression in wildtype, complemented strain *S. epidermidis* Δcap (capBCAD) and isogenic cap mutant strain (Δcap).
FIG. 2B shows scanning electron micrographs illustrating the detection of γPGA in wildtype, capBCAD and Δcap by anti-PGA antiserum.
FIG. 2C is a graph displaying the amounts of D-glutamic (D-Glu) and L-glutamic (L-Glu) acid detected by stereoselective chromatography and liquid chromatographic-mass spectrometric in wildtype, capBCAD and Δcap.

The nucleic acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. In the accompanying sequence listing:

SEQ ID NOs: 1-3 are representative oligonucleotide primer sequences utilized for real-time PCR analysis of cap expression.

SEQ ID NOs: 4-7 are representative oligonucleotide primer sequences employed for allelic replacement of the cap locus.

SEQ ID NOs: 8 and 9 are representative oligonucleotide primer sequences utilized for construction of complementation vectors.

SEQ ID NOs: 10-13 are representative oligonucleotide primer sequences used to confirm lack of cap expression in the cap mutant strain by real-time PCR.

SEQ ID NOs: 14-21 are illustrations of oligonucleotide primer sequences employed for amplification of the capB probe by Southern blot.

DETAILED DESCRIPTION OF SEVERAL EMBODIMENTS

I. Abbreviations
ADH: adipic acid dihydrazide
EF: edema factor
PGA: poly-γ-glutamic acid
γPGA: poly-γ-glutamic acid capsule
γDPGA: poly-γ-D-glutamic acid capsule
γLPGA: poly-γ-L-glutamic acid capsule
γDLPGA: poly-γ-D-L-glutamic acid capsule
GLC-MS: gas-liquid chromatography-mass spectrometry
LC-MS: liquid chromatography-mass spectrometry
MALDI-TOF: matrix-assisted laser desorption ionization time-of-flight
μg: microgram
μl: microliter
M: molar
NaCl sodium chloride
PA: protective antigen
PBS: phosphate buffered saline
PCR: polymerase chain reaction
PIA: polysaccharide intercellular adhesin
TSB: tryptic soy broth II. Terms
Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. Further, all Genbank references are incorporated by reference in their entirety as of their listings on Jul. 10, 2006. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Adjuvant: A substance that non-specifically enhances the immune response to an antigen. Development of vaccine adjuvants for use in humans is reviewed in Singh et al. (*Nat. Biotechnol.* 17:1075-1081, 1999), which discloses that, at the time of its publication, aluminum salts, such as aluminum hydroxide (Amphogel, Wyeth Laboratories, Madison, N.J.), and the MF59 microemulsion are vaccine adjuvants approved for human use.

In one embodiment, an adjuvant includes a DNA molecule with a motif that stimulates immune activation, for example the innate immune response or the adaptive immune response by T-cells, B-cells, monocytes, dendritic cells, and natural killer cells. Specific, non-limiting examples of a DNA motif that stimulates immune activation include CpG oligodeoxynucleotides, as described in U.S. Pat. Nos. 6,194,388; 6,207,646; 6,214,806; 6,218,371; 6,239,116; 6,339,068; 6,406,705; and 6,429,199. Another embodiment of an adjuvant is the carrier described herein.

Analog, Derivative or Mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibodies" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods and devices of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antigen: A compound, composition, or substance that may be specifically bound by the products of specific humoral or cellular immunity, such as an antibody molecule or T-cell receptor. In one embodiment, an antigen is a *Staphylococcus* antigen, such as γPGA.

*Bacillus*: A genus of bacteria whose collective features include degradation of most substrates derived from plant and animal sources, including cellulose, starch, pectin, proteins, agar, hydrocarbons, and others; antibiotic production; nitrification; denitrification; nitrogen fixation; facultative lithotrophy; autotrophy; acidophily; alkaliphily; psychrophily, thermophily and parasitism. Spore formation, universally found in the genus, is thought to be a strategy for survival in the soil environment, wherein the bacteria predominate. Aerial distribution of dormant spores likely explains the occurrence of *Bacillus* species in most habitats examined.

There are more than 40 recognized species in the genus *Bacillus* (Bergey's Manual of Systematic Bacteriology Vol. 2 (1986)). These include, but are not limited to, *B. acidocaldarius, B. alkalophilus, B. alvei, B. anthracis, B. azotoformans, B. badius, B. brevis, B. cereus, B. circulans, B. coagulans, B. fastidiosis, B. firmus, B. globisporus, B. insolitus, B. larvae, B. laterosporus, B. lentimorbus, B. lentus, B. licheniformis, B. macerans, B. macquariensis, B. marinus, B. megaterium, B. mycoides, B. pantothenticus, B. pasteurii, B. polymyxa, B. popillia, B. pumilus, B. schlegelii, B. sphaericus, B. stearothermophilus, B. subtilis*, and *B. thuringiensis*. In one specific, non-limiting example, a *Bacillus* is *Bacillus anthracis*, the agent that causes anthrax.

*Bacillus Anthracis*: The etiologic agent of anthrax, *Bacillus anthracis* is a large, gram-positive, nonmotile, spore-forming bacterial rod. The virulence of *B. anthracis* is dependent on anthrax toxin and the γDPGA capsule. The genes for the toxin, and the capsule, are carried by plasmids, designated pX01 and pX02, respectively (Mikesell et al., *Infect. Immun.* 39:371-76, 1983; Vodkin et al., *Cell* 34:693-97, 1983; Green et al., *Infect. Immun.* 49:291-97, 1985).

The γDPGA capsule of *B. anthracis* serves as an essential virulence factor during anthrax infection, inhibiting host defense mechanisms through inhibition of phagocytosis of the vegetative bacterial cells by macrophages. While other *Bacillus* produce γPGA in a mixture of both D- and L-forms, only *B. anthracis* is known to synthesize it exclusively in a D-conformation (Kovács et al., *J. Chem. Soc.* 4255-59, 1952). When injected into a subject, γDPGA has been shown to be a poor immunogen (Eisner, Schweiz. *Z. Pathol. Bakteriol.* 22:129-44, 1959; Ostroff et al., *Proc. Soc. Exp. Biol. Med.* 99:345-47, 1958). The capsule also shields the vegetative form of *B. anthracis* from agglutination by monoclonal antibodies that bind to or recognize its cell wall polysaccharide (Ezzell et al., *J. Clin. Microbiol.* 28:223-31, 1990).

Carrier: An immunogenic macromolecule to which an antigenic but not highly immunogenic molecule, such as, for example, a homopolymer of γPGA, can be bound. When bound to a carrier, the bound molecule becomes more immunogenic. Carriers are chosen to increase the immunogenicity of the bound molecule and/or to elicit antibodies against the carrier that are diagnostically, analytically, and/or therapeutically beneficial. Covalent linking of a molecule to a carrier confers enhanced immunogenicity and T-cell dependence (Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached.

Examples of bacterial products useful as carriers include bacterial toxins, such as *B. anthracis* protective antigen (including fragments that contain at least one antigenic epitope, and analogs or derivatives capable of eliciting an immune response), lethal factor and lethal toxin, and other bacterial toxins and toxoids, such as tetanus toxin/toxoid, diphtheria toxin/toxoid, *P. aeruginosa* exotoxin/toxoid, pertussis toxin/toxoid, and *C. perfringens* exotoxin/toxoid. Additional bacterial products for use as carriers include bacterial wall proteins and other products (for example, streptococcal or staphylococcal cell walls and LPS). Viral proteins, such as hepatitis B surface antigen and core antigen, can also be used as carriers, as well as proteins from higher organisms such as keyhole limpet hemocyanin, horseshoe crab hemocyanin, edestin, mammalian serum albumins, and mammalian immunoglobulins.

Covalent Bond: An interatomic bond between two atoms, characterized by the sharing of one or more pairs of electrons by the atoms. The terms "covalently bound" and "covalently linked" refer to making two separate molecules into one contiguous molecule. The terms in particular examples include reference to joining a γPGA polypeptide directly to a carrier molecule, and to joining a γPGA polypeptide indirectly to a carrier molecule, with an intervening linker molecule.

Epitope: An antigenic determinant. These are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Homopolymer: A polymer formed by the bonding together of multiple units of a single type of molecular species, such as a single monomer (for example, an amino acid).

Immune Response: A response of the immune system, such as by a B-cell, T-cell, macrophage or polymorphonucleocyte, to a stimulus such as an antigen. An immune response can include any cell of the body involved in a host defense response for example, an epithelial cell that secretes an interferon or a cytokine. An immune response includes, but is not limited to, an innate immune response or inflammation.

Immunogenic Conjugate or Composition: Terms used herein to mean a composition useful for stimulating or eliciting a specific immune response (or immunogenic response) in a vertebrate. In some embodiments, the immunogenic response is protective or provides protective immunity, in that it enables the vertebrate animal to better resist infection or disease progression that results from infection with the organism against which the immunogenic composition is directed.

In an embodiment, the immunogenic conjugate can be directed to a molecule instead of just an organism. For example, it is believed that an immunogenic response can arise from the generation of an antibody specific to one or more of the epitopes provided in the immunogenic composition. The response can include a T-helper or cytotoxic cell-based response to one or more of the epitopes provided in the immunogenic composition. All of these responses may originate from naïve or memory cells. A response can also include a production of cytokines. One specific example of a type of immunogenic composition is a vaccine. An immunogenic composition is also referred to as a immune-stimulating composition.

Immunogen: A compound, composition, or substance which is capable, under appropriate conditions, of stimulating an immune response, such as the production of antibodies or a T-cell response in an animal, including compositions that are injected or absorbed into an animal.

Immunologically Effective Dose: An immunologically effective dose is a therapeutically effective dose. For example, the γPGA conjugates of the disclosure are therapeutically effective and will prevent, treat, lessen, or attenuate the severity, extent or duration of a disease or condition such as an infection by S. epidermidis.

In-dwelling medical device: A device or medical implant which is to reside within a subject for an extended period of time (ranging from minutes to years). Examples of in-dwelling medical devices include, but are not limited to, catheters, artificial joints, pacemakers, and heart valves.

Inhibiting or Treating a Disease: Inhibiting the progressive or full development of a disease or condition in a subject who is at risk for infection with a pathogen such as S. epidermidis. "Treatment" refers to a therapeutic intervention that ameliorates a sign or symptom of a disease or pathological condition either before or after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" microorganism (such as a virus, bacterium, fungus, or protozoan) has been substantially separated or purified away from microorganisms of different types, strains, or species. Microorganisms can be isolated by a variety of techniques, including serial dilution and culturing.

An "isolated" biological component (such as a nucleic acid molecule, protein or organelle) has been substantially separated or purified away from other biological components in the cell of the organism in which the component naturally occurs, such as other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins, or fragments thereof.

Linker: A "chemical arm" between the protein, polypeptide or label and a drug or drug derivative. As one skilled in the art will recognize, to accomplish the requisite chemical structure, each of the reactants must contain the necessary reactive groups. Representative combinations of such groups are amino with carboxyl to formamide linkages, or carboxy with hydroxy to form ester linkages or amino with alkyl halides to form alkylamino linkages, or thiols with thiols to form disulfides, or thiols with maleimides or alkylhalides to form thioethers. Obviously, hydroxyl, carboxyl, amino and other functionalities, where not present may be introduced by known methods Likewise, as those skilled in the art will recognize, a wide variety of linking groups may be employed. The structure of the linkage should be a stable covalent linkage formed to attach the drug or drug derivative to the protein, polypeptide or label. In some cases the linking group can be designed to be either hydrophilic or hydrophobic in order to enhance the desired binding characteristics of the ligand and the receptor. The covalent linkages should be stable relative to the solution conditions under which the ligand and linking group are subjected. Generally preferred linking groups will be from 1-20 carbons and 0-10 heteroatoms (NH, O, S) and may be branched or straight chain. Without limiting the foregoing, it should be obvious to one skilled in the art that only combinations of atoms which are chemically compatible comprise the linking group. For example, amide, ester, thioether, thiol ester, keto, hydroxyl, carboxyl, ether groups in combinations with carbon-carbon bonds are acceptable examples of chemically compatible linking groups.

Opsonin: A macromolecule that becomes attached to the surface of a microbe and can be recognized by surface receptors of neutrophils and macrophages and that increases the efficiency of phagocytosis of the microbe. Opsonins include IgG antibodies, which are recognized by the Fcγ receptor on phagocytes, and fragments of complement proteins, which are recognized by CR1 (CD35) and by the leukocyte integrin Mac-1.

Opsonophagocytosis: The process of attaching opsonins to microbial surfaces to target the microbes for phagocytosis. For example, the elicited immune response include opsonophagocytic activity.

PGA: A homopolymer of glutamic acid residues in the L-form or the D-form or a combination thereof.

γPGA: A homopolymer of glutamic acid residues linked by γ peptide bonds. The glutamic acid residues constituting the γPGA homopolymer can be solely in the L-form (γLPGA) or the D-form (γDPGA) or a combination thereof (γDLPGA).

γDLPGA: A homopolymer of glutamic acid residues which includes a combination of the L-form (γLPGA) and the D-form (γDPGA). In an example, the L-form (γLPGA) and the D-form (γDPGA) are presented at substantially equal amounts (40-60% of each of the D- and L-form of γPGA).

Pharmaceutically Acceptable Vehicles: The pharmaceutically acceptable vehicles useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more SARS-CoV nucleic acid molecules, proteins or antibodies that bind these proteins, and additional pharmaceutical agents.

In general, the nature of the vehicle will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid vehicles can include, for example, pharmaceutical grades of mannitol, lactose, starch, or magnesium stearate. In addition to biologically-neutral vehicles, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide. Conservative amino acid substitutions are those substitutions that, when made, least interfere with the properties of the original protein, that is, the structure and especially the function of the protein is conserved and not significantly changed by such substitutions. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Purified: The term "purified" does not require absolute purity; rather, it is intended as a relative term. Thus, for example, a purified peptide, protein, γPGA conjugate, or other active compound is one that is isolated in whole or in part from naturally associated proteins and other contaminants, in which the peptide, protein, γPGA conjugate, or other active compound is purified to a measurable degree relative to its naturally occurring state, for example, relative to its purity within a cell extract or chemical synthesis checker.

In certain embodiments, the term "substantially purified" refers to a peptide, protein, γPGA conjugate, or other active compound that has been isolated from a cell, cell culture medium, or other crude preparation and subjected to fractionation to remove various components of the initial preparation, such as proteins, cellular debris, and other components. Such purified preparations can include materials in covalent association with the active agent, such as glycoside residues or materials admixed or conjugated with the active agent, which may be desired to yield a modified derivative or analog of the active agent or produce a combinatorial therapeutic formulation, conjugate, fusion protein or the like. The term purified thus includes such desired products as peptide and protein analogs or mimetics or other biologically active compounds wherein additional compounds or moieties are bound to the active agent in order to allow for the attachment of other compounds and/or provide for formulations useful in therapeutic treatment or diagnostic procedures.

Generally, substantially purified peptides, proteins, γPGA conjugates, or other active compounds include more than 80% of all macromolecular species present in a preparation prior to admixture or formulation of the respective compound with additional ingredients in a complete pharmaceutical formulation for therapeutic administration. Additional ingredients can include a pharmaceutical carrier, excipient, buffer, absorption enhancing agent, stabilizer, preservative, adjuvant or other like co-ingredients. More typically, the peptide, protein, γPGA conjugate or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are less than 1%.

Recombinant Nucleic Acid: A nucleic acid sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques such as those described in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989. The term recombinant includes nucleic acids that have been altered solely by addition, substitution, or deletion of a portion of the nucleic acid.

Specific Binding Agent: A "specific binding agent" is an agent that binds substantially only to a defined target. Thus a protein-specific binding agent binds substantially only the defined protein, or to a specific region within the protein. As used herein, "specific binding agent" includes antibodies and other agents that bind substantially to a specified polypeptide. The antibodies may be monoclonal or polyclonal antibodies that are specific for the polypeptide, as well as immunologically effective portions ("fragments") thereof.

The determination that a particular agent binds substantially only to a specific polypeptide may readily be made by using or adapting routine procedures. One suitable in vitro assay makes use of the Western blotting procedure (described in many standard texts, including Harlow and Lane, *Using Antibodies: A Laboratory Manual*, CSHL, New York, 1999).

Staphylococci: Staphylococci are gram-positive spherical bacteria that occur in microscopic clusters and produce exotoxins. In 1884, Rosenbach described two pigmented colony types of staphylococci and proposed the appropriate nomenclature: *Staphylococcus aureus* (yellow) and *Staphylococcus albus* (white). The latter species is now named *Staphylococcus epidermidis*. Although more than 20 species of *Staphylococcus* exist, only *Staphylococcus aureus* (*S. aureus*) and *Staphylococcus epidermidis* (*S epidermidis*) are significant in their interactions with humans. *S. aureus* colonizes mainly in the nasal passages, but it may be found regularly in most other anatomical locales. *S. epidermidis* is an inhabitant of the skin and mucous membrane of warm-blooded animals.

*S. aureus* forms a fairly large yellow colony on rich medium. By comparison, *S. epidermidis* forms a relatively small white colony. *S. aureus* is often hemolytic on blood agar while *S. epidermidis* is non-hemolytic. Staphylococci are facultative anaerobes that grow by aerobic respiration or by fermentation that yields principally lactic acid. The bacteria are catalase-positive and oxidase-negative. *S. aureus* can grow at a temperature range of 15 to 45° C. and at NaCl concentrations as high as 15 percent. Nearly all strains of *S. aureus* produce the enzyme coagulase. In contrast, nearly all strains of *S. epidermidis* lack this enzyme. Thus, strains of *S. epidermidis* are often referred to as coagulase-negative staphylococci.

Although most strains of *S. epidermidis* are nonpathogenic and may even play a protective role in their host as normal flora, *S. epidermidis* has become the most prevalent pathogen involved in hospital-acquired infections. For example, this member of the coagulase-negative group of staphylococci can cause severe infection after penetration of the epidermal protective barriers of the human body. Further, it is frequently resistant to common antibiotics (Vuong, C., and Otto, M. *Microbes Infect.* 4:481-489, 2002).

Therapeutically Effective Amount: A quantity of a specified agent sufficient to achieve a desired effect in a subject being treated with that agent. For example, this may be the amount of a γPGA conjugate useful in increasing resistance to, preventing, ameliorating, and/or treating infection and disease caused by a coagulase-negative *Staphylococcus*, and/or a γPGA expressing *Staphylococcus*, such as a *S. epidermidis* infection in a subject. Ideally, a therapeutically effective amount of an agent is an amount sufficient to increase resistance to, prevent, ameliorate, and/or treat infection and disease such as is caused by *S. epidermidis* infection in a subject without causing a substantial cytotoxic effect in the subject. The effective amount of an agent useful for increasing resistance to, preventing, ameliorating, and/or treating infection and disease in a subject will be dependent on the subject being treated, the severity of the affliction, and the manner of administration of the therapeutic composition.

Toxoid: A nontoxic derivative of a bacterial exotoxin produced, for example, by formaldehyde or other chemical treatment. Toxoids are useful in the formulation of immunogenic compositions because they retain most of the antigenic properties of the toxins from which they were derived.

III. Description of Several Embodiments

Coagulase-negative staphylococci, including the species *S. epidermidis*, are the predominant cause of hospital-acquired infections. Treatment is especially difficult owing to biofilm formation and frequent antibiotic resistance. Further, virulence mechanisms of these important opportunistic pathogens have remained poorly characterized.

The present disclosure provides important novel biological functions for γPGA and demonstrates that γPGA (such as γDLPGA) is an excellent target for drugs or vaccines aimed at preventing and/or treating disease caused by *S. epidermidis* and related staphylococci pathogens. Notably, γDLPGA was synthesized by all tested strains of *S. epidermidis* and a series of closely related coagulase-negative staphylococci, most of which are opportunistic pathogens. Although PGA has a generally low immunogenicity, recent studies have shown that anti-PGA antibodies efficiently protect from anthrax infection in animal models (Leppla, S. H., Robbins, J. B., Schneerson, R., and Shiloach, J. *J. Clin. Invest.* 110: 141-144, 2002; Schneerson, R., et al. *Proc. Natl. Acad. Sci. U.S.A.* 100: 8945-8950, 2003; Kozel T. R., et al. *Proc. Natl. Acad. Sci. U.S.A.* 101: 5042-5047, 2003; and Rhie, G. E., et al. *Proc. Natl. Acad. Sci. U.S.A.* 100: 10925-10930, 2003). The present studies indicate that anti-PGA antibodies (such as antibodies produced by an immunogenic composition) are valuable for the treatment of chronic infections by *S. epidermidis* and certain other pathogenic staphylococci. Hence antisera containing a therapeutically effective amount of these antibodies can be administered to a subject to treat the infection, or an immune response against the target can be stimulated to provide a similar antimicrobial effect. In particular embodiments, the antibodies are directed against γDLPGA.

A. *Staphylococcus* γPGA Polypeptide Polypeptides and Conjugates

*Staphylococcus* capsular γPGA polypeptide conjugates are disclosed, as are *Staphylococcus* capsular γPGA polypeptides that include, but are not limited to, γDLPGA polypeptides. However in all examples throughout, γDLPGA can be substituted for γPGA. Further, in all examples throughout, *Staphylococcus* can be substituted with *S. epidermidis, S. capitis, S. warneri, S. saccharolyticus, S. caprae, S. hominis, S. haemolyticus, S. lugdunensis, S. simulans* or *S. epidermidis*. The present disclosure provides compositions that comprise or consist or consist essentially of γPGA polypeptides (such as γDLPGA polypeptides) or antibodies against these polypeptides (such as antisera). The polypeptides or antisera can be provided in substantially purified forms, for example at least 90% or 95% of the composition comprises the polypeptide or antisera. In certain examples at least 90% or 95% of the composition comprises γDLPGA polypeptides or antisera against it. The compositions may also include a pharmaceutical vehicle and/or an adjuvant.

γPGA is an anionic, extracellular polymer, in which the α-amino and γ-carboxy groups of D- or L-glutamic acid are linked by isopeptide bonds. *Staphylococcus* produces γPGA as a mixture of both the D- and L-forms (see FIG. 2C), whereas other bacilli such as *B. anthracis* have been previously noted to produce exclusively γDPGA. In one embodiment, the γPGA conjugates disclosed herein are γLPGA conjugates. In another embodiment, the γPGA conjugates are γDPGA conjugates. In a further embodiment, the γPGA conjugates are mixtures of γLPGA conjugates and γDPGA conjugates (a γDLPGA conjugate). For example, the γLPGA conjugates and γDPGA are present in substantially equal amounts in certain compositions. In an embodiment, substantially equal amounts can include approximately fifty percent of each isoform±approximately twenty percent, that is, about 30% to 70% of one or the other.

Staphylococcus capsular γPGA polypeptides can be isolated and purified by many methods well known in the art, such as salt fractionation, phenol extraction, precipitation with organic solvents (for example, hexadecyltrimethylammonium bromide (cetavlon) or ethanol), affinity chromatography, ion-exchange chromatography, hydrophobic chromatography, high performance liquid chromatography, gel filtration, isoelectric focusing, and the like. In one specific, non-limiting example, capsular γDLPGA polypeptides are extracted from the culture supernatant of growing bacilli by acid precipitation. (Kocianova, C. et al. *J. Clin. Invest.* 115: 688-694, 2005). The presence of extracted γPGA polypeptides is confirmed by methods well known in the art, including immuno-dot blot assays. Further, enantiomeric confirmations of the γPGA polypeptides are determined by stereoselective chromatography and liquid chromatographic-mass spectrometric detection of glutamic acid.

It is contemplated that synthetic γPGA polypeptides of varying lengths (for example, about 5, 10, 15, or 20 residues) having either or both of the D- or L-configuration can be readily synthesized by automated solid phase procedures well known in the art. Suitable syntheses can be performed by utilizing "T-boc" or "F-moc" procedures. Techniques and procedures for solid phase synthesis are described in Solid Phase Peptide Synthesis: A Practical Approach, by E. Atherton and R. C. Sheppard, published by IRL, Oxford University Press, 1989. In specific, non-limiting examples, the synthetic γPGA polypeptide includes about 1 to about 20 glutamic acid residues, such as about 10 to about 15 glutamic acid residues, or about 10 glutamic acid residues. The compositions and purity of synthetic γPGA polypeptides can be determined by GLC-MS and matrix-assisted laser desorption ionization time-of-flight (MALDI-TOF) spectrometry.

In an embodiment, the conjugate includes a Staphylococcus capsular γDLPGA polypeptide linked to a carrier. Carriers for linking to γPGA polypeptides as disclosed herein are chosen to increase the immunogenicity of the γPGA polypeptides and/or to elicit antibodies against the carrier which are diagnostically, analytically, and/or therapeutically beneficial. Covalent linking of γPGA polypeptides to a carrier confers enhanced immunogenicity and T-cell dependence of the resultant immune response. Useful carriers include polymeric carriers, which can be natural, semi-synthetic or synthetic materials containing one or more functional groups, for example primary and/or secondary amino groups, azido groups, hydroxyl groups, or carboxyl groups, to which a reactant moiety can be attached. The carrier can be water soluble or insoluble, and in some embodiments is a protein or polypeptide. Carriers that fulfill these criteria are generally known in the art (see, for example, Fattom et al., *Infect. Immun.* 58:2309-12, 1990; Devi et al., *PNAS* 88:7175-79, 1991; Szu et al., *Infect. Immun.* 59:4555-61, 1991; Szu et al., *J. Exp. Med.* 166:1510-24, 1987; and Pavliakova et al., *Infect. Immun.* 68:2161-66, 2000).

Specific, non-limiting examples of water soluble polypeptide carriers include, but are not limited to, natural, semi-synthetic or synthetic polypeptides or proteins from bacteria or viruses. In one embodiment, bacterial products for use as carriers include bacterial wall proteins and other products (for example, LPS of Gram-negative bacteria), and soluble antigens of bacteria. In another embodiment, bacterial products for use as carriers include bacterial toxin or toxoids derived therefrom. Bacterial toxins include bacterial products that mediate toxic effects, inflammatory responses, stress, shock, chronic sequelae, or mortality in a susceptible host. Specific, non-limiting examples of bacterial toxins include, but are not limited to: *B. anthracis* PA (for example, as encoded by bases 143779 to 146073 of GenBank Accession No. NC 007322, herein incorporated by reference as listed on Jul. 10, 2006) and variants of PA that share at least 90%, at least 95%, or at least 98% amino acid sequence homology to this reference PA, fragments thereof that contain at least one antigenic epitope, and analogs or derivatives capable of eliciting an immune response; *B. anthracis* LF (for example, as encoded by the complement of bases 149357 to 151786 of GenBank Accession No. NC 007322 herein incorporated by reference as listed on Jul. 10, 2006); bacterial toxins and toxoids, such as tetanus toxin/toxoid (for example, as described in U.S. Pat. Nos. 5,601,826 and 6,696,065); diphtheria toxin/toxoid (for example, as described in U.S. Pat. Nos. 4,709,017 and 6,696,065); *P. aeruginosa* exotoxin/toxoid/ (for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); and *C. perfringens* exotoxin/toxoid (for example, as described in U.S. Pat. Nos. 5,817,317 and 6,403,094). Viral proteins, such as hepatitis B surface antigen (for example, as described in U.S. Pat. Nos. 5,151,023 and 6,013,264) and core antigen (for example, as described in U.S. Pat. Nos. 4,547,367 and 4,547,368) can also be used as carriers, as well as proteins from higher organisms such as keyhole limpet hemocyanin, horseshoe crab hemocyanin, edestin, mammalian serum albumins, and mammalian immunoglobulins.

In addition to bacterial and viral products, polysaccharide carriers can also be useful in preparing the γPGA polypeptide conjugates as disclosed herein. Polysaccharide carriers include, but are not limited to, dextran, capsular polysaccharides from microorganisms such as the Vi capsular polysaccharide from *S. typhi* (see, for example, U.S. Pat. No. 5,204,098); *Pneumococcus* group 12 (12F and 12A) polysaccharides; *Haemophilus influenzae* type d polysaccharide; and certain plant, fruit, and synthetic oligo- or polysaccharides which are immunologically similar to capsular polysaccharides, such as pectin, D-galacturonan, oligogalacturonate, or polygalacturonate (for example, as described in U.S. Pat. No. 5,738,855).

Specific, non-limiting examples of water insoluble carriers useful in preparing the γPGA polypeptide conjugates as disclosed herein include, but are not limited to, aminoalkyl agarose (for example, aminopropyl or aminohexyl SEPHAROSE; Pharmacia Inc., Piscataway, N.J.), aminopropyl glass, cross-linked dextran, and the like, to which a reactive moiety can be attached. Other carriers can be used, provided that a functional group is available for covalently attaching a reactive group.

Binding of γPGA polypeptides to a carrier can be direct or via a linker element. Linkers can include amino acids, including amino acids capable of forming disulfide bonds, but can also include other molecules such as, for example, polysaccharides or fragments thereof. Linkers can be chosen so as to elicit their own immunogenic effect which may be either the same, or different, than that elicited by the γPGA polypeptides and/or carriers disclosed herein. For example, such linkers can be bacterial antigens which elicit the production of antibodies to an infectious bacteria. In such instances, for example, the linker can be a protein or protein fragment of an infectious bacterium.

The covalent linking of the γPGA polypeptides to the carrier can be carried out in any manner well known to one of skill in the art. Conjugation methods applicable to the present disclosure include, by way of non-limiting example, reductive amination, diazo coupling, thioether bond, disulfide bond, amidation and thiocarbamoyl chemistries. In one embodiment, the γPGA polypeptides and/or the carrier are "activated" prior to conjugation or linking. Activation provides the necessary chemical groups for the conjugation reaction to occur. In one specific, non-limiting example, the activation step includes derivatization with adipic acid dihydrazide (ADH). In another specific, non-limiting example, the activation step includes derivatization with the N-hydroxysuccinimide ester of 3-(2-pyridyl dithio)-propionic acid (SPDP). In yet another specific, non-limiting example, the activation step includes derivatization with succinimidyl 3-(bromoacetamido) propionate (SBAP). Further, non-limiting examples of derivatizing agents include succinimidylformylbenzoate (SFB) and succinimidyllevulinate (SLV).

Following conjugation of a γPGA polypeptide to a carrier, the γPGA polypeptide-carrier conjugate can be purified by a variety of techniques well known to one of skill in the art. One goal of the purification step is to remove unbound γPGA polypeptide from the γPGA polypeptide-carrier conjugate. One method for purification, involving ultrafiltration in the presence of ammonium sulfate, is described in U.S. Pat. No. 6,146,902. Alternatively, γPGA polypeptide-carrier conjugates can be purified away from unreacted γPGA polypeptide and carrier by any number of standard techniques including, for example, size exclusion chromatography, density gradient centrifugation, hydrophobic interaction chromatography, or ammonium sulfate fractionation. See, for example, Anderson et al., *J. Immunol.* 137:1181-86, 1986 and Jennings & Lugowski, *J. Immunol.* 127:1011-18, 1981. The compositions and purity of the conjugates can be determined by GLC-MS and MALDI-TOF spectrometry.

For γPGA conjugates or compositions including γPGA polypeptides bound at one point to a carrier, complex structural characteristics can be used to determine optimal immunogenicity for synthetic conjugates (see, for example, Kabat, *Prog. Immunol.* 5:67-85, 1983; Pozsgay et al., *PNAS* 96:5194-97, 1999; Lee et al., *J. Immunol.* 116:1711-18, 1976; and Dintzis et al., *PNAS* 73:3671-75, 1976). γPGA polypeptide lengths must be sufficient to occupy a cognate antibody combining site. In addition, the density of the γPGA polypeptide on the carrier influences the ability of the γPGA conjugate to form both aggregates with the surface Ig receptor, and to permit interaction of the carrier fragments with T-cells. For example, γPGA conjugates having a density of γPGA polypeptide chains to carrier molecule of between about 5:1 to about 32:1, respectively, such as about 8:1 to about 22:1, or about 10:1 to about 15:1, are contemplated to be useful within the immunogenic compositions and methods described herein.

In an embodiment, an immunogenic composition may include *Bacillus* capsular γPGA polypeptide covalently linked to a carrier in combination with or in lieu of *Staphylococcus* capsular γPGA polypeptide and an adjuvant. For example, the immunogenic composition may include a *Bacillus* capsular γPGA polypeptide covalently linked to a carrier as disclosed in WO 2005/000884 A1, published Jan. 6, 2005, which is incorporated herein by reference in its entirety.

The disclosed immune conjugates can elicit immune responses in a subject. For example, the immune response may include opsonophagocytic activity. Further, the conjugates or other therapeutic compositions can be administered to a subject who has been diagnosed with a coagulase-negative *staphylococcus*-induced infection, such as an *S. epidermidis* infection, for example a subject in whom a diagnosis has been made by laboratory culture. Alternatively the subject may be one who is at risk of such an infection, for example a hospitalized subject with an in-dwelling device, such as a catheter. The therapeutic effect of the disclosed compositions can either inhibit the development or progression of the infection, hence they can be administered either prophylactically or to treat an existing infection.

B. Specific Binding Agents

The disclosure contemplates use of specific binding agents that bind a γPGA polypeptide of *Staphylococcus*, or a γPGA conjugate (for example a γDLPGA conjugate) as disclosed herein. The binding agent can be used to purify and detect the γPGA polypeptides, as well as for detection and diagnosis of *Staphylococcus* infections. Further, the binding agent can be used to treat a *Staphylococcus* infection such as by treating a subject with an antiserum against γPGA, such as an antiserum against γDLPGA. Examples of the binding agents include a polyclonal or monoclonal antibody (including humanized monoclonal antibody), and fragments thereof, that bind to any of the γPGA polypeptides or γPGA conjugates disclosed herein such as γDLPGA.

Monoclonal or polyclonal antibodies can be raised to recognize the target, such as γPGA polypeptide and/or conjugate as described herein, or an analog or derivative thereof. Substantially pure conjugate suitable for use as immunogen can be prepared as described above. Monoclonal or polyclonal antibodies to the conjugate can then be prepared.

Monoclonal antibodies to the polypeptides can be prepared from murine hybridomas according to the classic method of Kohler & Milstein (*Nature* 256:495-97, 1975), or a derivative method thereof. Briefly, a mouse is repetitively inoculated with a few micrograms of the selected immunogen (for example, a γPGA conjugate) over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as the enzyme-linked immunoabsorbent assay (ELISA), as originally described by Engvall (*Meth. Enzymol.,* 70:419-39, 1980), or a derivative method thereof. Selected positive clones can be expanded and their monoclonal antibody product harvested for use. Detailed procedures for monoclonal antibody production are described in Harlow and Lane, *Using Antibodies: A Laboratory Manual*, CSHL, New York, 1999. Polyclonal antiserum containing antibodies can be prepared by immunizing suitable animals with an immunogen comprising a γPGA conjugate.

Effective antibody production (whether monoclonal or polyclonal) is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.,* 33:988-91, 1971).

Booster injections can be given at regular intervals, and antiserum harvested when the antibody titer thereof, as determined semi-quantitatively, for example, by double immunodiffusion in agar against known concentrations of the antigen, begins to fall. See, for example, Ouchterlony et al., *Handbook of Experimental Immunology*, Wier, D. (ed.), Chapter 19, Blackwell, 1973. A plateau concentration of antibody is usually in the range of 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

Antibodies can be contained in blood plasma, serum, hybridoma supernatants and the like. Alternatively, the antibodies can be isolated to the extent desired by well known techniques in the art, such as, ion exchange chromatography, sizing chromatography, or affinity chromatography. The antibodies can be purified so as to obtain specific classes or subclasses of antibody, such as IgM, IgG, IgA, IgG1, IgG2, IgG3, IgG4 and the like. Antibodies of the IgG class are of use for purposes of passive protection.

Antibody fragments can be used in place of whole antibodies and can be readily expressed in prokaryotic host cells. Methods of making and using immunologically effective portions of monoclonal antibodies, also referred to as "antibody fragments," are well known and include those described in Better & Horowitz (*Methods Enzymol.* 178:476-96, 1989; Glockshuber et al., *Biochemistry* 29:1362-67, 1990) and U.S. Pat. Nos. 5,648,237; 4,946,778; and 5,455,030. Conditions whereby a polypeptide/binding agent complex can form, as well as assays for the detection of the formation of a polypeptide/binding agent complex and quantitation of binding affinities of the binding agent and polypeptide, are standard in the art. Such assays can include, but are not limited to, Western blotting, immunoprecipitation, immunofluorescence, immunocytochemistry, immunohistochemistry, fluorescence activated cell sorting, fluorescence in situ hybridization, immunomagnetic assays, ELISA, ELISPOT (Coligan et al., *Current Protocols in Immunology*, Wiley, NY, 1995), agglutination assays, flocculation assays, cell panning, and the like, as are well known to one of skill in the art.

The γPGA antibodies or antibody fragments disclosed herein can have a number of diagnostic and therapeutic uses. For example, the antibodies or antibody fragments can be used for passive immunotherapy, such as by administering to a subject a therapeutically effective amount of the antibody or antibody fragments. In another example, the antibodies or antibody fragments can be used as in vitro diagnostic agents in various immunoassays to test for the presence of *Staphylococcus* expressing a γPGA polypeptide in biological (for example, clinical) samples or on surfaces such as an in-dwelling device surface. Useful immunoassays include, but are not limited to, agglutination assays, radioimmunoassays, ELISA, fluorescence assays, Western blots and the like. In one such assay, for example, the biological sample is contacted first with an antibody which binds *Staphylococcus* γPGA polypeptide, and then with a labeled second antibody to detect the presence of a *Staphylococcus*, to which the first antibody has bound. Such assays can be, for example, of direct format (where a labeled first antibody is reactive with the γDLPGA polypeptide), an indirect format (where a labeled second antibody is reactive with the first antibody), a competitive format (such as the addition of a labeled γDLPGA polypeptide), or a sandwich format (where both labeled and unlabelled antibody are utilized), as well as other formats well known to one of skill in the art.

Binding agents of this disclosure can be bound to a substrate (for example, beads, tubes, slides, plates, nitrocellulose sheets, and the like) or conjugated with a detectable moiety, or both bound and conjugated. The detectable moieties contemplated for the present disclosure can include, but are not limited to, an immunofluorescent moiety (for example, fluorescein, rhodamine), a radioactive moiety (for example, $^{32}$P, $^{125}$I, $^{35}$S), an enzyme moiety (for example, horseradish peroxidase, alkaline phosphatase), a colloidal gold moiety, and a biotin moiety. Such conjugation techniques are standard in the art (for example, see Harlow and Lane, *Using Antibodies: A Laboratory Manual*, CSHL, New York, 1999; Yang et al., *Nature*, 382:319-24, 1996).

D. Pharmaceutical and Immunogenic Compositions and Uses Thereof

Pharmaceutical compositions (including therapeutic and prophylactic formulations) of a γPGA conjugate are also encompassed by the present disclosure, and include a γDLPGA conjugate and/or other biologically active agent as described herein, typically combined together with one or more pharmaceutically acceptable vehicles and, optionally, other therapeutic ingredients (for example, antibiotics, or anti-inflammatories).

Within the pharmaceutical compositions and methods of the disclosure, the conjugate and/or other biologically active agent can be administered to subjects by a variety of mucosal administration modes, including by oral, rectal, intranasal, intrapulmonary, or transdermal delivery, or by topical delivery to other surfaces. Optionally, the conjugate and/or other active agent can be administered by non-mucosal routes, including by intramuscular, subcutaneous, intravenous, intraatrial, intra-articular, intraperitoneal, or parenteral routes. In other embodiments, the conjugate and/or other active agent can be administered ex vivo such as directly to an in-dwelling medical device.

To formulate pharmaceutical compositions of the present disclosure, the conjugate and/or other biologically active agent can be combined with various pharmaceutically acceptable additives, as well as a base or vehicle for dispersion of the conjugate and/or other biologically active agent. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton Ind.) and IL-12 (Genetics Institute, Cambridge Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The disclosed conjugate and/or other biologically active agent can be dispersed in a base or vehicle, which can include a hydrophilic compound having a capacity to disperse the conjugate and/or other biologically active agent, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including, fluid or viscous solutions, gels, pastes, powders, microspheres and films for direct application to a mucosal surface.

The conjugate and/or other biologically active agent can be combined with the base or vehicle according to a variety of methods, and release of the conjugate and/or other biologically active agent can be by diffusion, disintegration of the vehicle, or associated formation of water channels. In some circumstances, the conjugate and/or other biologically active agent is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time. In other embodiments the active agent is provided in a substantially pure form, excluding other components usually found in bacteria. The active agent may be at least 50%, 75%, 90% or 95% pure, in that it is purified from a naturally occurring biological background.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the γPGA conjugate, polypeptide or antisera (such as the γDLPGA conjugate, polypeptide or antisera) and/or other biologically active agent can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the conjugate and/ or other biologically active agent can be brought about by including in the composition an agent which delays absorption, for example, monostearate salts and gelatin.

In certain embodiments, the agent can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the conjugate and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly (D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the conjugate and/or other biologically active agent in the required amount in an appropriate solvent with one or a combination of ingredients enumerated herein, as required, followed by filtered sterilization. Generally, dispersions are prepared by incorporating the conjugate and/or other biologically active agent into a sterile vehicle that contains a basic dispersion medium and the required other ingredients from those enumerated herein. In the case of sterile powders, methods of preparation include vacuum drying and freeze-drying which yields a powder of the γPGA conjugate and/or other biologically active agent plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the active agent can be delivered to a subject in a manner consistent with conventional methodologies associated with management of the disorder for which treatment or prevention is sought. In accordance with the disclosure herein, a prophylactically or therapeutically effective amount of the active agent is administered to a subject in need of such treatment for a time and under conditions sufficient to prevent, inhibit, and/or ameliorate a selected disease, condition or one or more symptom(s) thereof. For example, a therapeutically effective amount of the active agent is administered to a subject to treat an S. epidermidis infection.

Typical subjects intended for treatment with the compositions and methods of the present disclosure include humans, as well as non-human primates and other animals. To identify subjects for prophylaxis or treatment according to the methods of the disclosure, accepted screening methods are employed to determine risk factors associated with a targeted or suspected disease of condition (for example, S. epidermidis infection) as discussed herein, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize disease-associated markers. These and other routine methods allow the clinician to select patients in need of therapy using the methods and pharmaceutical compositions of the disclosure. In accordance with these methods and principles, the active agents disclosed herein can be administered according to the teachings herein as an independent prophylaxis or treatment program, or as a follow-up, adjunct or coordinate treatment regimen to other treatments, including surgery, vaccination, immunotherapy, hormone treatment, cell, tissue, or organ transplants, and the like.

The conjugates can be used in coordinated vaccination protocols or combinatorial formulations with immunogens to enhance an immune response elicited by the immunogen alone. In one example, novel combinatorial immunogenic compositions and coordinated immunization protocols employ separate immunogens or formulations, each directed toward eliciting an anti-immunogen or an anti-γPGA (such as an anti-γDLPGA) immune response. Separate immunogens that elicit the anti-immunogen or anti-γPGA immune response can be combined in a polyvalent immunogenic composition administered to a subject in a single immunization step, or they can be administered separately (in monovalent immunogenic compositions) in a coordinate immunization protocol. Typically, when the anti-immunogen and anti-γPGA immunogens are administered separately, they are administered coordinately, in close temporal sequence (for example, the anti-PA immunogen will be administered hours, one or two days, or within a week or two, prior to administration of the anti-γPGA immunogen, or vice versa).

The administration of the conjugate and/or other biologically active agent of the disclosure can be for either prophylactic or therapeutic purpose. When provided prophylactically, the conjugate and/or other biologically active agent is provided in advance of any symptom. The prophylactic administration of the conjugate and/or other biologically active agent serves to prevent or ameliorate any subsequent infection. When provided therapeutically, the conjugate and/or other biologically active agent is provided at (or shortly after) the onset of a symptom of disease or infection. The conjugate and/or other biologically active agent of the disclosure can thus be provided prior to the anticipated exposure to S. epidermidis or another Staphylococcus, so as to attenuate the anticipated severity, duration or extent of an infection and/or associated disease symptoms, after exposure or suspected exposure to the bacteria, or after the actual initiation of an infection.

For prophylactic and therapeutic purposes, the active agents presently disclosed can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the conjugate and/or other biologically active agent can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, immunologic and histopathologic assays). One advantage to using in vitro models is only ordinary calculations and adjustments are required to determine an appropriate concentration and dose to administer a therapeutically effective amount of the conjugate and/or other biologically active agent. For example, a therapeutically effective amount is effective to elicit a desired immune response or alleviate one or more symptoms of a targeted disease. In another example, an effective amount or effective dose of the conjugate and/or biologically active agent may simply inhibit or enhance one or more selected biological activities correlated with a disease or condition, as set forth herein, for either therapeutic or diagnostic purposes.

The actual dosage of the conjugate and/or other biologically active agent (such as anti-sera) will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the conjugate and/or other biologically active agent for eliciting the desired activity or biological response in the subject. Dosage regimens can be adjusted to provide an optimum prophylactic or therapeutic response. A therapeutically effective amount is also one in which any toxic or detrimental side effects of the γPGA conjugate (such as the γDLPGA conjugate) and/or other biologically active agent is outweighed in clinical terms by therapeutically beneficial effects. A non-limiting range for a therapeutically effective amount of the conjugate and/or other biologically active agent within the methods and formulations of the disclosure is about 0.01 mg/kg body weight to about 10 mg/kg body weight, such as about 0.05 mg/kg to about 5 mg/kg body weight, or about 0.2 mg/kg to about 2 mg/kg body weight. The antibodies of the present disclosure will typically be administered in a dosage ranging from about 1 mg/kg body weight to about 10 mg/kg body weight of the subject, although a lower or higher dose can be administered.

Upon administration of a conjugate or related immunogenic composition of the disclosure (for example, via injection, aerosol, oral, topical or other route), the immune system of the subject typically responds to the immunogenic composition by producing antibodies specific for γPGA and/or a carrier protein. Such a response signifies that an immunologically effective dose of the conjugate or related immunogenic composition was delivered. An immunologically effective dosage can be achieved by single or multiple administrations (including, for example, multiple administrations per day), daily, or weekly administrations. For each particular subject, specific dosage regimens can be evaluated and adjusted over time according to the individual need and professional judgment of the person administering or supervising the administration of the conjugate and/or other biologically active agent. In some embodiments, the antibody response of a subject administered the compositions of the disclosure will be determined in the context of evaluating effective dosages/immunization protocols. In most instances it will be sufficient to assess the antibody titer in serum or plasma obtained from the subject. Decisions as to whether to administer booster inoculations and/or to change the amount of the composition administered to the individual can be at least partially based on the antibody titer level. The antibody titer level can be based on, for example, an immunobinding assay which measures the concentration of antibodies in the serum which bind to a specific antigen, for example, γDLPGA. The ability to neutralize in vitro and in vivo biological effects of the *S. epidermidis* can also be assessed to determine the effectiveness of the treatment.

Dosage can be varied by the attending clinician to maintain a desired concentration at a target site (for example, the lungs or systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth. To achieve the same serum concentration level, for example, slow-release particles with a release rate of 5 nanomolar (under standard conditions) would be administered at about twice the dosage of particles with a release rate of 10 nanomolar.

It is contemplated that delivery of the conjugates can be enhanced by methods and agents that target selective transport mechanisms and promote endo- or transcytocis of macromoloecular drugs.

In this regard, the compositions and delivery methods of the disclosure optionally incorporate a selective transport-enhancing agent that facilitates transport of one or more biologically active agents. These transport-enhancing agents can be employed in a combinatorial formulation or coordinate administration protocol with one or more of the peptides, proteins, analogs and mimetics disclosed herein, to coordinately enhance delivery of the biologically active agent(s) into target cells. Exemplary selective transport-enhancing agents for use within this aspect of the disclosure include, but are not limited to, glycosides, sugar-containing molecules, and binding agents such as lectin binding agents, which are known to interact specifically with epithelial transport barrier components (see, for example, Goldstein et al., *Annu. Rev. Cell. Biol.* 1:1-39, 1985). For example, specific "bioadhesive" ligands, including various plant and bacterial lectins, which bind to cell surface sugar moieties by receptor-mediated interactions can be employed as carriers or conjugated transport mediators for enhancing delivery of conjugates within the disclosure. Certain bioadhesive ligands for use within the disclosure will mediate transmission of biological signals to epithelial target cells that trigger selective uptake of the adhesive ligand by specialized cellular transport processes (endocytosis or transcytosis). These transport mediators can therefore be employed as a "carrier system" to stimulate or direct selective uptake of the conjugate within the methods of the disclosure. To utilize these transport-enhancing agents, general carrier formulation and/or conjugation methods known in the art are used to complex or otherwise coordinately administer a selective transport enhancer (for example, a receptor-specific ligand) and the conjugate to trigger or mediate enhanced endo- or transcytosis of the γPGA conjugate (such as the γDLPGA conjugate) into specific target cell(s), tissue(s) or compartment(s).

Lectins are plant proteins that bind to specific sugars found on the surface of glycoproteins and glycolipids of eukaryotic cells. Concentrated solutions of lectins have a "mucotractive" effect, and various studies have demonstrated rapid receptor mediated endocytosis of lectins and lectin conjugates (for example, concanavalin A conjugated with colloidal gold particles) across mucosal surfaces. Additional studies have reported that the uptake mechanisms for lectins can be utilized for intestinal drug targeting in vivo. In certain of these studies, polystyrene nanoparticles (500 nm) were covalently coupled to tomato lectin and reported yielded improved systemic uptake after oral administration to rats. In addition to plant lectins, microbial adhesion and invasion factors provide a rich source of candidates for use as adhesive/selective transport carriers within the compositions and methods of the disclosure (see, for example, Lehr, *Crit. Rev. Therap. Drug Carrier Syst.* 11:177-218, 1995 and Swann, *Pharmaceutical Research* 15:826-32, 1998). Two components are necessary for bacterial adherence processes, a bacterial "adhesin" (adherence or colonization factor) and a receptor on the host cell surface. Bacteria causing mucosal infections need to penetrate the mucus layer before attaching themselves to the epithelial surface. This attachment is usually mediated by bacterial fimbriae or pilus structures, although other cell surface components can also take part in the process. Adherent bacteria colonize mucosal epithelia by multiplication and initiation of a series of biochemical reactions inside the target cell through signal transduction mechanisms (with or without the help of toxins).

Associated with these invasive mechanisms, a wide diversity of bioadhesive proteins (for example, invasin, internalin) originally produced by various bacteria and viruses are known. These allow for extracellular attachment of such microorganisms with an impressive selectivity for host species and even particular target tissues. Signals transmitted by such receptor-ligand interactions trigger the transport of intact, living microorganisms into, and eventually through, epithelial cells by endo- and transcytotic processes. Such naturally occurring phenomena can be harnessed (for example, by complexing a γPGA conjugate with an adhesin according to the teachings herein for enhanced delivery of the conjugates and/or other biologically active compounds. One advantage of this strategy is that the selective carrier partners thus employed are substrate-specific, leaving the natural barrier function of epithelial tissues intact against other solutes (see, for example, Lehr, *Drug Absorption Enhancement*, pp. 325-362, de Boer, Ed., Harwood Academic Publishers, 1994).

Various bacterial and plant toxins that bind epithelial surfaces in a specific, lectin-like manner are also useful within the methods and compositions of the disclosure. For example, diphtheria toxin enters host cells rapidly by receptor mediated endocytosis. Likewise, the B subunit of the *E. coli* heat labile toxin binds to the brush border of intestinal epithelial cells in a highly specific, lectin-like manner. Uptake of this toxin and transcytosis to the basolateral side of the enterocytes has been reported in vivo and in vitro. Other researches have expressed the transmembrane domain of diphtheria toxin in *E. coli* as a maltose-binding fusion protein and coupled it chemically to high-Mw poly-L-lysine. The resulting complex was successfully used to mediate internalization of a reporter gene in vitro. In addition to these examples, *Staphylococcus aureus* produces a set of proteins (for example, staphylococcal enterotoxin A, staphylococcal enterotoxin B and toxic shock syndrome toxin 1) which act both as superantigens and toxins. Studies relating to these proteins have reported dose-dependent, facilitated transcytosis of staphylococcal enterotoxin B and toxic shock syndrome toxin 1 in Caco-2 cells.

Various plant toxins, mostly ribosome-inactivating proteins, have been identified that bind to any mammalian cell surface expressing galactose units and are subsequently internalized by receptor mediated endocytosis. Toxins such as nigrin b, sarcin, ricin and saporin, viscumin, and modeccin are highly toxic upon oral administration (that is, they are rapidly internalized). Therefore, modified, less toxic subunits of these compounds will be useful within the disclosure to facilitate the uptake of the conjugates and other biologically active agents, other bacterial products and analogs, variants, derivatives and mimetics thereof.

Viral hemagglutinins include another type of transport agent to facilitate delivery of γPGA conjugates (such as the γDLPGA conjugate) and other biologically active agents within the methods and compositions of the disclosure. The initial step in many viral infections is the binding of surface proteins (hemagglutinins) to mucosal cells. These binding proteins have been identified for most viruses, including rotaviruses, *Varicella zoster* virus, semliki forest virus, adenoviruses, potato leafroll virus, and reovirus. These and other exemplary viral hemagglutinins can be employed in a combinatorial formulation (for example, a mixture or conjugate formulation) or coordinate administration protocol with, for example, one or more γPGA conjugates, PA immunogens, other bacterial products, or analogs, variants, derivatives and mimetics thereof. Alternatively, viral hemagglutinins can be employed in a combinatorial formulation or coordinate administration protocol to directly enhance delivery of the conjugate or other biologically active agent within the disclosure.

A variety of endogenous, selective transport-mediating factors are also available for use with the disclosure. Exemplary among these are protocytotic transport carriers within the folate carrier system, which mediate transport of the vitamin folic acid into target cells via specific binding to the folate receptor (see, for example, Reddy et al., *Crit. Rev. Ther. Drug Car. Syst.* 15:587-27, 1998). This receptor system has been used in drug-targeting approaches to cancer cells, but also in protein delivery, gene delivery, and targeting of antisense oligonucleotides to a variety of cell types. Folate-drug conjugates are well suited for use within the methods and compositions of the disclosure, because they allow penetration of target cells exclusively via folate receptor-mediated endocytosis. When folic acid is covalently linked to a biologically active agent, folate receptor binding affinity (KD~10-10M) is not significantly compromised, and endocytosis proceeds relatively unhindered, promoting uptake of the attached active agent by the folate receptor-expressing cell.

In addition to the folate receptor pathway, a variety of additional methods to stimulate transcytosis within the disclosure are directed to the transferrin receptor pathway, and the riboflavin receptor pathway. In one aspect, conjugation of a γPGA conjugate (such as the γDLPGA conjugate) or other biologically active agent to riboflavin can effectuate receptor mediated endocytosis uptake. Yet additional embodiments of the disclosure utilize vitamin B12 (cobalamin) as a specialized transporter (for example, conjugation partner) to facilitate entry of the conjugates and other biologically active agents into target cells. Certain studies suggest that this particular system can be employed for mucosal delivery into the intestine. Still other embodiments of the disclosure utilize transferrin as a carrier or stimulant of receptor mediated endocytosis of mucosally delivered biologically active agents. Transferrin, an 80 kDa iron-transporting glycoprotein, is efficiently taken up into cells by receptor mediated endocytosis. Transferrin receptors are found on the surface of most proliferating cells, in elevated numbers on erythroblasts and on many kinds of tumors. Each of the foregoing agents that stimulate receptor-mediated transport can be employed within the methods of the disclosure as combinatorially formulated (for example, conjugated) and/or coordinately administered agents to enhance receptor-mediated transport of the conjugates and other biologically active agents, including, PA, carriers, linkers, and other bacterial toxins and analogs, variants, derivatives and mimetics thereof.

Immunoglobulin transport mechanisms provide yet additional endogenous pathways and reagents for enhancing delivery of active agents within the methods and compositions of the disclosure. Receptor-mediated transcytosis of immunoglobulin G (IgG) across the neonatal small intestine serves to convey passive immunity to many newborn mammals. Within the methods and compositions of the present disclosure, IgG and other immune system-related carriers (including polyclonal and monoclonal antibodies and various fragments thereof) can be complexed or otherwise coordinately administered with the conjugates and other biologically active agents to provide for targeted delivery, typically by receptor-mediated transport. For example, the conjugate or other biologically active agent can be covalently linked to the IgG or other immunological active agent or, alternatively, formulated in liposomes or other carrier vehicle which is in turn modified (for example, coated or covalently linked) to incorporate IgG or other immunological transport enhancer. In certain embodiments, polymeric IgA and/or IgM transport agents are employed, which bind to the polymeric immunoglobulin receptors of target epithelial cells. Within these methods, expression of polymeric immunoglobulin receptors can be enhanced by cytokines.

Within more detailed aspects of the disclosure, antibodies and other immunological transport agents can be themselves modified for enhanced delivery of the conjugates or other biologically active agents. For example, antibodies can be more effectively administered within the methods and compositions of the disclosure by charge modifying techniques. In one such aspect, an antibody drug delivery strategy involving antibody cationization is utilized that facilitates both trans-endothelial migration and targeted cell endocytosis (see, for example, Pardridge, et al., *JPET* 286:548-44, 1998). In one such strategy, the pI of the antibody is increased by converting surface carboxyl groups of the protein to extended primary amino groups. These cationized homologous proteins have no measurable tissue toxicity and have minimal immunogenicity. In addition, monoclonal antibodies can be cationized with retention of affinity for the target protein.

Additional selective transport-enhancing agents for use within the disclosure include whole bacteria and viruses, including genetically engineered bacteria and viruses, as well as components of such bacteria and viruses. This aspect of the disclosure includes the use of bacterial ghosts and subunit constructs, for example, as described by Huter et al., *J. Control. Rel.* 61:51-63, 1999. Bacterial ghosts are non-denatured bacterial cell envelopes, for example as produced by the controlled expression of the plasmid-encoded lysis gene E of bacteriophage PhiX174 in gram-negative bacteria. Protein E-specific lysis does not cause any physical or chemical denaturation to bacterial surface structures, and bacterial ghosts are therefore useful in development of inactivated whole-cell vaccines. Ghosts produced from *Actinobacillus pleuropneumoniae, Pasteurella haemolytica* and *Salmonella* sp. have proved successful in vaccination studies. Recombinant bacterial ghosts can be created by the expression of foreign genes fused to a membrane-targeting sequence, and thus can carry foreign therapeutic peptides and proteins anchored in their envelope. The fact that bacterial ghosts preserve a native cell wall, including bioadhesive structures like fimbriae of their living counterparts, makes them suitable for the attachment to specific target tissues such as mucosal surfaces. Bacterial ghosts have been shown to be readily taken up by macrophages, thus adhesion of ghosts to specific tissues can be followed by uptake through phagocytes.

In view of the foregoing, a wide variety of ligands involved in receptor-mediated transport mechanisms are known in the art and can be variously employed within the methods and compositions of the disclosure (for example, as conjugate partners or coordinately administered delivery enhancers) to enhance delivery or receptor-mediated transport of γPGA conjugates and other biologically active agents, including bacterial products. Generally, these ligands include hormones and growth factors, bacterial adhesins and toxins, lectins, metal ions and their carriers, vitamins, immunoglobulins, whole viruses and bacteria or selected components thereof. Exemplary ligands among these classes include, for example, calcitonin, prolactin, epidermal growth factor, glucagon, growth hormone, estrogen, lutenizing hormone, platelet derived growth factor, thyroid stimulating hormone, thyroid hormone, cholera toxin, diphtheria toxin, *E. coli* heat labile toxin, Staphylococcal enterotoxins A and B, ricin, saporin, modeccin, nigrin, sarcin, concanavalin A, transcobalantin, catecholamines, transferrin, folate, riboflavin, vitamin B1, low density lipoprotein, maternal IgO, polymeric IgA, adenovirus, vesicular stomatitis virus, Rous sarcoma virus, *V. cholerae, Kiebsiella strains, Serratia* strains, parainfluenza virus, respiratory syncytial virus, Varicella zoster, and *Enterobacter* strains (see, for example, Swann, *Pharmaceutical Research* 15:826-32, 1998).

In certain additional embodiments of the disclosure, membrane-permeable peptides (for example, "arginine rich peptides") can be employed to facilitate delivery of γDLPGA conjugates or other biologically active agents of the disclosure. (See WO 2005/000884 A1, published Jan. 6, 2005). While the mechanism of action of these peptides remains to be fully elucidated, they provide useful delivery enhancing adjuncts for use within the compositions and methods herein.

The methods of using γPGA conjugates and the related compositions and methods of the disclosure, are useful in increasing resistance to, preventing, ameliorating, and/or treating infection and disease caused by *Staphylococcus* in animal hosts, and other, in vitro applications. For example, the methods and compositions are useful in increasing resistance to, preventing, ameliorating, and/or treating infection and disease caused by *S. epidermidis* infection in animals and humans. These immunogenic compositions can be used for active immunization for prevention of *S. epidermidis* infection, and for preparation of immune antibodies. In one embodiment, the therapeutic compositions and methods are designed to confer specific immunity against infection with *S. epidermidis*, and to induce antibodies specific to *S. epidermidis* γDLPGA. The therapeutic compositions are composed of non-toxic components, suitable for infants, children of all ages, and adults.

The methods of the disclosure are broadly effective for treatment (including prevention) of an *S. epidermidis* infection or other related staphylococci infections. In selected embodiments, one or more symptoms or associated effects of exposure to and/or infection with *S. epidermidis* can be prevented or otherwise treated by administration to a mammalian subject at risk of *S. epidermidis* infection, or presenting with one or more *Staphylococcus* symptom(s), of an effective amount of an immunogenic γPGA composition (such as the γDLPGA composition) of the disclosure. Therapeutic compositions and methods of the disclosure for prevention or treatment of toxic or lethal effects of bacterial infection are applicable to a wide spectrum of infectious agents. Any significant reduction or preventive effect of the composition with respect to the foregoing disease condition(s) or symptom(s) administered constitutes a desirable, effective property of the subject composition/method of the disclosure.

The compositions and methods of the disclosure are particularly useful for treatment and prevention of infection of exposure to *S. epidermidis* and/or other disease- or illness-causing staphylococci. Additional embodiments of the disclosure are directed to diagnostic compositions and methods to identify individuals at risk for exposure, infection, or long term deleterious effects of exposure to pathogenic bacteria, for example *S. epidermidis*. In additional aspects of the disclosure, the methods and compositions disclosed herein are useful for identification of environmental agents, including *S. epidermidis* and other staphylococci expressing a γPGA. Methods and compositions of the disclosure are employed to detect, and alternatively to treat and/or ameliorate, such ubiquitous environmental exposures and associated symptoms. For example, antibodies of the disclosure provide for screening for γDLPGA in mammalian subjects at risk of contact/infection with *S. epidermidis*.

In related embodiments, the disclosure provides compositions, including but not limited to, mammalian serum, plasma, and immunoglobulin fractions, which contain antibodies that are immunoreactive with a γDLPGA of *S. epidermidis* or another *Staphylococcus* species or strain. These antibodies and antibody compositions can be useful to treat (including prevent), and/or otherwise ameliorate infection and disease caused by the microorganism. The disclosure also provides such antibodies in isolated form. In exemplary embodiments, high titer anti-γDLPGA sera, antibodies isolated therefrom, or monoclonal antibodies, can be used for therapeutic treatment for patients with infection by *S. epidermidis* or another *Staphylococcus* species or strain. Antibodies elicited by the agents of this disclosure can be used for the treatment of established *S. epidermidis* or other *Staphylococcus* infections, and can also be useful in providing passive protection to an individual exposed to *S. epidermidis* or another *Staphylococcus*, such as a coagulase-negative *Staphylococcus*.

The instant disclosure also includes kits, packages and multi-container units containing the herein described pharmaceutical compositions, active ingredients, and/or means for administering the same for use in the prevention and treatment of S. epidermidis and other Staphylococcus diseases and other conditions in mammalian subjects. Kits for diagnostic use are also provided. These kits may include a container or formulation that contains one or more of the γPGA conjugates and/or other active agent described herein to detect S. epidermidis infection. For example, the composition is formulated in a pharmaceutical preparation for delivery to a subject. The γPGA conjugate (such as the γDLPGA conjugate) and/or other biologically active agent is/are optionally contained in a bulk dispensing container or unit or multi-unit dosage form. Optional dispensing methods may be provided, for example a pulmonary or intranasal spray applicator. Packaging materials optionally include a label or instruction indicating for what treatment purposes (for example, S. epidermidis) and/or in what manner the pharmaceutical agent packaged therewith can be used.

The subject matter of the present disclosure is further illustrated by the following non-limiting Examples.

EXAMPLE 1

Materials and Methods

Bacterial Strains, Growth Conditions, and Basic Molecular Biology Methods.

The clinical isolate S. epidermidis 1457 (Mack, D., et al. Infect. Immun. 62: 3244-3253, 1994) was used in this study. Bacteria were grown in tryptic soy broth (TSB) unless otherwise noted. Antibiotics were used at the following concentrations: chloramphenicol, 10 μg/ml; spectinomycin, 100 μg/ml; and ampicillin, 100 μg/ml. Cultures were incubated at 37° C. with shaking at 200 rpm. DNA manipulation, isolation of plasmid DNA, and transformation of Escherichia coli were performed using standard procedures. Staphylococcal plasmid DNA was prepared with the Qiagen Plasmid Midi Kit as described (Vuong, C., Gerke, C., Somerville, G. A., Fischer, E. R., and Otto, M. J. Infect Dis. 188: 706-718, 2003). S. epidermidis was transformed by electroporation as described (Augustin, J., et al. Eur. J. Biochem. 204: 1149-1154, 1992). Polymerase chain reactions (PCRs) were performed with Ready-To-Go PCR Beads (Amersham Biosciences) as recommended by the manufacturer. DNA was sequenced using Big Dye Terminator cycle sequencing (version 3.0) on an ABI3700 sequencer (Applied Biosystems). Nucleotide sequences were analyzed using the program Vector NTI Suite (InforMax). Primers for DNA amplifications by PCR were purchased from Sigma Genosys. The following oligonucleotides were used in this study for TaqMan analysis of cap expression: capF (SEQ ID NO: 1), capProbe (SEQ ID NO: 2), and capR (SEQ ID NO: 3). For allelic replacement of the cap locus, primers CapEco (SEQ ID NO: 4), CapBam (SEQ ID NO: 5), CapSal (SEQ ID NO: 6), and CapHind (SEQ ID NO: 7) were employed. In the construction of complementation vectors studies, oligoprimers capBam2 (SEQ ID NO: 8) and capXba (SEQ ID NO: 9) were utilized. To confirm the lack of cap expression in the cap mututant strain by real-time PCR, the following primers were used: CAP1 (SEQ ID NO: 10), CAP2 (SEQ ID NO: 11), C2P1 (SEQ ID NO: 12) and C2P5 (SEQ ID NO: 13). Amplification of the capB probe for the Southern blot assays utilized the following primers: CapSB2 (SEQ ID NO: 14), CapSB3 (SEQ ID NO: 15), CapSB-D3 (SEQ ID NO: 16), CapSB-D4 (SEQ ID NO: 17), CapSB-A1 (SEQ ID NO: 18), CapSB-A2 (SEQ ID NO: 19), CapSB-C1 (SEQ ID NO: 20), and CapSB-D4 (SEQ ID NO: 21). The 74 strains used for epidemiological studies were obtained from N. El Solh (Institut Pasteur, Paris, France) and are predominantly nonclonal (Galdbart, J. O., Morvan, A., Desplaces, N., and El Solh, N. J. Clin. Microbiol. 37: 1306-1312, 1999).

Real-Time PCR.

RNA isolation was performed using a FastPrep BLUE Kit (Q-BioGene Inc.). Oligonucleotide primers and probes were designed using Primer Express 2.0 software (Applied Biosystems). The probe used for analysis of cap expression was located within the capB gene. TaqMan analysis was performed in a 384-well MicroAmp Optical using a 7900 Sequence Detector (Applied Biosystems). Standard curves were determined with purified chromosomal template DNA at concentrations ranging from 0.001 ng/ml to 10 ng/ml. Assays were performed in triplicate using cDNA samples, and 16S rRNA as control, with a standard cycle protocol.

Southern Blot Analysis.

Equal amounts of EcoRV-digested genomic DNA were separated by gel electrophoresis on a 0.7% agarose gel and visualized by ethidium bromide staining. DNA was transferred onto a nylon membrane (GE Osmonics Labstore) and probed with digoxigenin-labeled PCR product amplified from the capB or capD genes of S. epidermidis 1457 or with a cocktail of probes amplified from the capA, capB, capC, and capD genes. Prehybridization, hybridization, posthybridization, and immunologic detection were performed as described in the technical update accompanying the nonradioactive DNA Labeling and Detection Kit (Roche Applied Science). For immunologic detection, the membrane was incubated with a 1:5,000 dilution of sheep anti-digoxigenin Fab fragments conjugated to alkaline phosphatase. Probe-target hybrids were detected using the chromogenic substrate nitroblue tetrazolium/5-bromo-4-chloro-3-indolyl phosphate.

Immuno-Dot Blot Assay.

Surface-attached γDLPGA was released from the cell surface by boiling bacteria for 30 minutes at 100° C. or by autoclaving. γDLPGA was then purified by acid precipitation as described in Hariby E. E., and Rydon, H. N. Biochemistry. 40: 297-307, 1946. Aliquots (3 μl) of the samples were spotted on a nitrocellulose membrane, air-dried, and γDLPGA was detected with anti-γDLPGA antiserum using a scanner and Total Lab Version 2003 software (Nonlinear USA). The assay was calibrated by serial dilution of the most intensive sample. The value detected in the wild-type strain was set to 100% and production values in the other strains were expressed relative to that value. Anti-γDLPGA antiserum (kindly provided by R. Schneerson, National Institute of Child Health & Human Development, NIH, Bethesda, Md., USA) was developed against PGA from Bacillus pumilus. For Staphylococcus strains other than S. epidermidis, a strain with a signal higher than that of the background of the S. epidermidis Δcap mutant was considered a PGA producer.

Construction of an Isogenic Cap Deletion Mutant and Cap-Complementing Vector.

To delete capBCAD in S. epidermidis 1457, PCR-amplified regions flanking the cap locus and a spectinomycin resistance cassette were cloned into plasmid pBT2 (Brückner, R. FEMS Microbiol. Lett. 151: 1-8, 1997), yielding plasmid pBTΔcap, which was used for allelic replacement as described (Vuong, C., Gotz, F., and Otto, M. Infect. Immun. 68: 1048-1053, 2000). The proper integration of the resistance gene marker spc was verified by direct sequencing of the genomic DNA at the borders of the PCR-derived regions. Lack of cap transcript in the cap mutant strain was verified by real-time PCR. S. epidermidis 1457 in which capBCAD was deleted was named S. epidermidis Δcap. To complement for capBCAD in S. epidermidis Δcap, capBCAD genes were cloned into plasmid pRB474 (Brückner, R. *FEMS Microbiol. Lett.* 151: 1-8, 1997). The resulting plasmid was named pRB-capBCAD.

Purification of γDLPGA and Detection of D- and L-Glutamic Acid.

Cultures were grown in TSB medium supplemented with 1 M NaCl to induce γDLPGA production. γDLPGA was first purified as described above. Then, γDLPGA samples were further purified by ion exchange chromatography using a RESOURCE Q 6 ml column (Amersham Biosciences) on an AKTA Purifier 10 (Amersham Biosciences) and a gradient from 0.2% acetic acid to 0.2% acetic acid/1 M NaCl in 20 column volumes at a flow rate of 5 ml/min. Fractions with positive reaction in an immuno-dot blot were combined, dialyzed against water, lyophilized, resuspended in 6 M HCl, and hydrolyzed at 110° C. for 24 hours. Samples were lyophilized again and dissolved in 200 µl of water. Ten microliters of the samples were then injected onto a Chirobiotic T column (Astec) using 0.1% triethylammonium acetate (pH 4.0) in 80% ethanol as elution buffer at a flow rate of 0.4 ml/min. Chromatography was performed using an Agilent 1100 series HPLC connected to a VL Trap mass spectrometer. The extracted ion chromatograms at 146 Da, the mass of glutamic acid, were used to determine the amounts of D- and L-glutamic acid by peak integration in comparison to pure D- and L-glutamic acid.

Isolation of Human Polymorphonuclear Leukocytes and Phagocytosis Experiments.

Human polymorphonuclear leukocytes (PMNs) were isolated from heparinized venous blood of healthy individuals with a standard method (Voyich, J. M., et al. *Proc. Natl. Acad. Sci. U.S.A.* 100: 1996-2001, 2003). All studies were performed in accordance with a protocol approved by the Institutional Review Board for Human Subjects of NIAID. Cell preparations contained approximately 99% PMNs and all reagents used contained <25.0 pg/ml endotoxin. Phagocytosis of *S. epidermidis* by human PMNs was analyzed by flow cytometry with a previously described method (Voyich, J. M., et al. *Proc. Natl. Acad. Sci. U.S.A.* 100: 1996-2001, 2003). Briefly, bacteria were cultured to stationary growth phase, washed in PBS, and labeled with fluorescein-5-isothiocyanate for 15 minutes. PMNs ($10^6$/100 µl) and bacteria ($2 \times 10^7$/100 µl) were combined in wells of serum-coated 96-well round-bottom microtiter plates. Plates were incubated for 30 minutes at 37° C. and the degree of phagocytosis was determined by flow cytometry.

Peptide Bacterial Killing Assays.

*S. epidermidis* cultures were harvested, washed with PBS buffer, and resuspended in 10 mM sodium phosphate buffer (pH 7.0). Bacterial killing assays were performed using a final concentration of approximately $10^5$ *S. epidermidis* cells in each sample. Antimicrobial peptides were dissolved in the following solutions: human β-defensin 3, 10 mM acetic acid, and LL-37, 10% acetonitrile with 0.1% trifluoroacetic acid. The bacteria were exposed to a range of antimicrobial peptide concentrations (0, 5, 10, 20, 30, and 40 µg/ml). An equal volume of the respective peptide dilution buffer was applied to control samples. Samples were incubated at 37° C. for 2 hours and appropriate dilution series of the samples were plated on TSB agar. Survivor *S. epidermidis* cells were enumerated after 24 hours of incubation at 37° C. The percentage of killed *S. epidermidis* was calculated using the formula $(1-[CFU_{peptide}/CFU_{control}]) \times 100$.

Scanning Immunoelectron Microscopy.

Fifty-microliter aliquots of *S. epidermidis* cultures were washed with PBS buffer. Cells were resuspended in 200 µl of anti-γDLPGA antiserum and incubated at 37° C. with agitation at 400 rpm for 12 hours. Samples were washed with PBS and pellets were subsequently incubated with goat anti-rabbit IgG conjugated with 20 nm of gold (BB International) at 37° C. with agitation at 400 rpm for 2 hours. Following antibody labeling, the cell suspensions were attached to coverslips, fixed with 2.5% glutaraldehyde in 0.1 M sodium cacodylate, and post-fixed with 1% osmium tetroxide in 0.1 M sodium cacodylate. Samples were washed with distilled water, dehydrated in a graded ethanol series, critical-point dried under $CO_2$ with a Bal-Tec model cpd 030 drier (Balzers), mounted on aluminum studs, and sputter-coated with 100 angstroms of chromium in a model IBS/TM200S ion beam sputterer (South Bay Technologies) prior to viewing at 10 kV on a Hitachi S-4500 field emission scanning electron microscope (Hitachi) in backscatter imaging mode.

Murine Model of Device-Related Infection.

Female Balb/c mice were used in a model of subcutaneous implanted device-related infection as described (Kadurugamuwa, J. L., et al. *Infect. Immun.* 71:882-890, 2003). Two catheter pieces of 1-cm length were placed under the skin of the dorsum of each animal. CFUs on catheters were counted before insertion and were in the range of $2 \times 10^5$ on all implanted catheters. CFU on excised catheters and surrounding tissues were counted after 1 week of infection. All studies were performed in accordance with a protocol approved by the Animal Care and Use Committee of Rocky Mountain Laboratories, NIAID.

Statistics and DNA Sequence Analysis.

Statistical analysis was performed using GraphPad Prism version 4.0. DNA sequences were compared using Clustal W software.

EXAMPLE 2

Molecular Genetic Comparison of Bacteria with Genes Encoding a Putative PGA Synthesis Machinery This example demonstrates that the *S. epidermidis* genome contains the genes that code for PGA synthesis.

Only recently, it was discovered that the biofilm exopolysaccharide polysaccharide intercellular adhesin (PIA) protects *S. epidermidis* from major mechanisms of innate host defense (Vuong, C., et al. *Cell. Microbiol.* 6: 269-275, 2004). However, PIA is restricted to a subpopulation of *S. epidermidis*, and therefore, a ubiquitous principle protecting *S. epidermidis* from innate host defense has remained elusive. Thus, the recently published *S. epidermidis* genome (Zhang, Y. Q., et al. *Mol. Microbiol.* 49:1577-1593, 2003) was searched for gene loci potentially involved in such protection. Phylogenetic trees were constructed based on sequence comparisons of the capB (amide ligase), capC (unknown function), and capD (depolymerase) genes. CapA is a putative PGA exporter. A comparison of capA genes (putative PGA exporters) was excluded because capA homologs were not found in all the organisms and comparison of transporters is normally less indicative of phylogenetic relations. The resulting phylogenetic trees are presented in FIG. 1A. Of the microorganisms shown, production of PGA has been demonstrated previously only in *B. anthracis* and *B. subtilis*.

Figure 3:
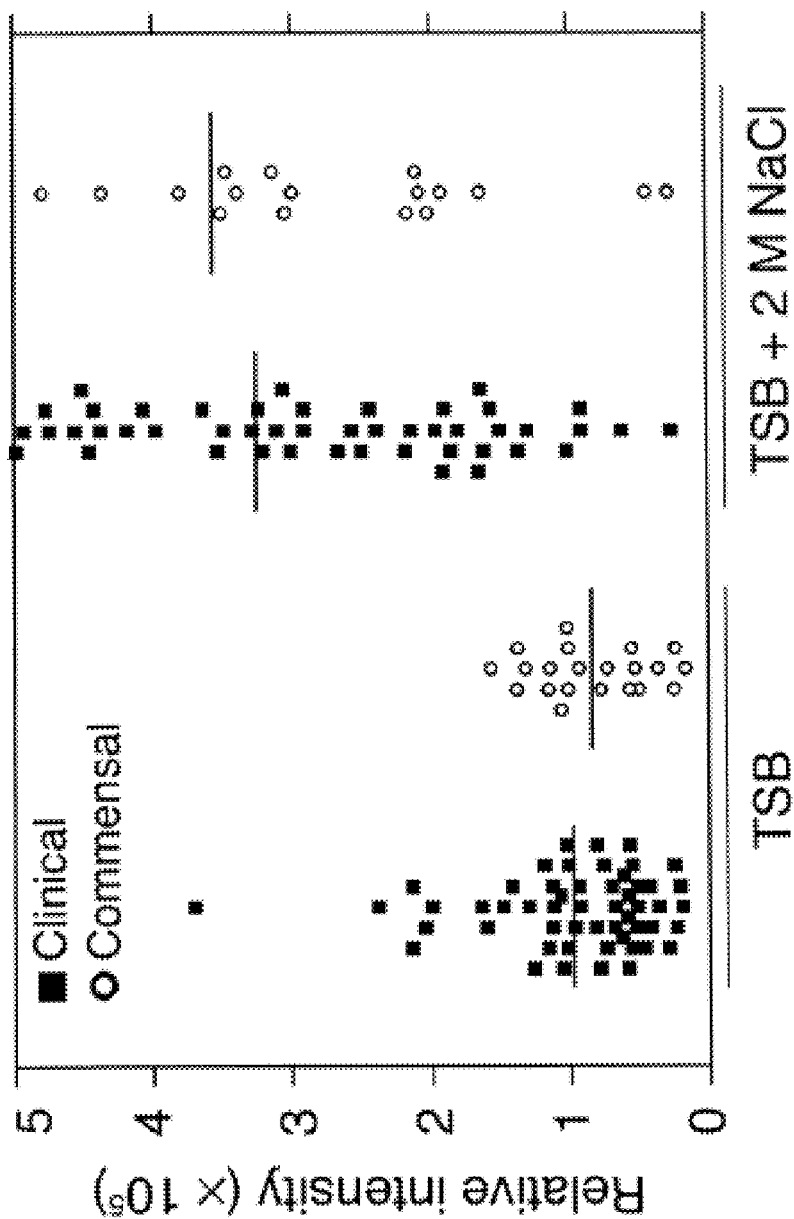
FIG. 3 is a graph demonstrating γPGA expression in *S. epidermidis* strains of clinical and commensal origin under low and high salt (2 M NaCl) conditions.
Figures 4A, 4B, 4C:
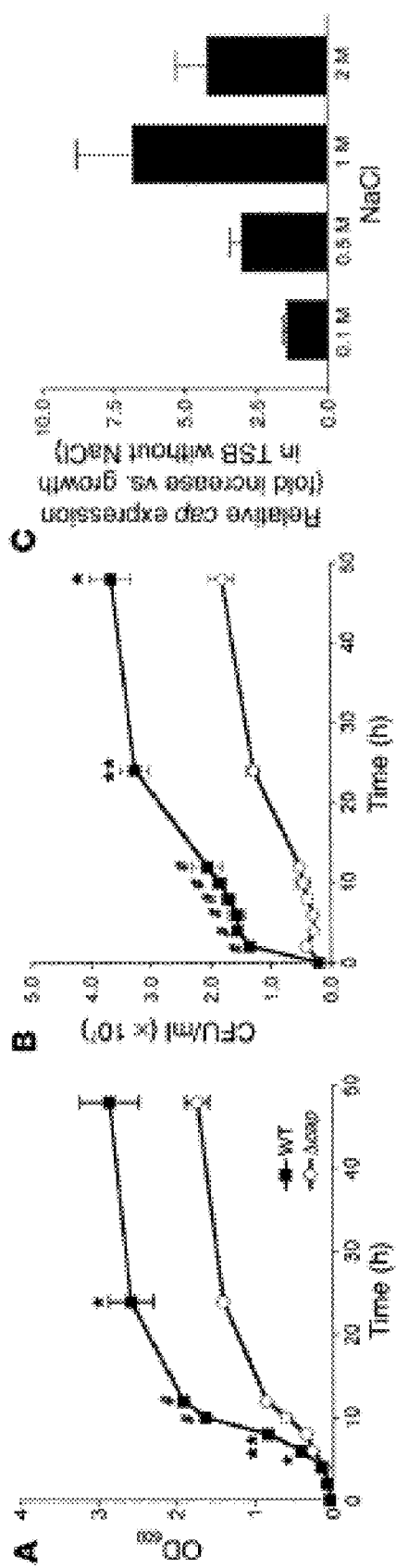
FIG. 4A is a graph depicting the growth ($OD_{600}$) of wildtype and cap mutant strains in Luria-Bertani medium supplemented with 2 M NaCl.
FIG. 4B is a graph displaying the viability (CFU) of wildtype and cap mutant strains in Luria-Bertani medium supplemented with 2 M NaCl.
FIG. 4C is a graph representing NaCl inducibility of cap expression measured by quantitative real-time PCR analysis.

As illustrated in FIG. 1A, in contrast to its relative *S. aureus*, *S. epidermidis* has the cap locus that codes for production of the anionic exopolymer PGA. Further, the *S. epidermidis* cap genes show high similarity to those of *B. anthracis* and *B. subtilis*. In addition, as demonstrated in FIG. 1B, in contrast to *B. subtilis* and several human pathogens that have parts of the cap genes, the genetic organization of the cap locus of *B. anthracis* is well conserved in *S. epidermidis*. Of note, the *B. anthracis* cap gene cluster is located on a plasmid and flanked by IS231 insertion sequences. All other genes are located in the bacterial chromosomes.

EXAMPLE 3

PGA Production in *S. epidermidis*

This example demonstrates that the *S. epidermidis* cap gene locus drives production of surface-attached PGA.

In FIGS. 2A-2C, Δcap represents the isogenic cap deletion strain. Further, capBCAD is the complemented strain *S. epidermidis* Δcap (pRBcapBCAD).

To analyze the role of the cap genes in *S. epidermidis*, a deletion mutant (*S. epidermidis* Δcap) was constructed, in which the entire cap locus was replaced by a spectinomycin resistance cassette. To complement the mutant, the cap operon was cloned with its natural promoter in a plasmid and transformed the mutant with that plasmid (pRBcapBCAD). PGA production was determined in the mutant, wild-type, and complemented strains. Real-time PCR data indicated that the cap genes in *S. epidermidis* are expressed. Accordingly, relative expression of PGA was determined by immuno-dot blot analysis. PGA was extracted from bacterial cell surfaces as described in Example 1: Methods. A calibration curve was obtained by dilution of the most intensive sample obtained from the PGA-overexpressing complemented strain *S. epidermidis* Δcap (pRBcapBCAD). Results are the mean±SEM of 4 experiments for the samples and the mean±SEM of 4 different serial dilutions for the calibration curve. A representative blot is shown at the top of FIG. 2A. As illustrated in FIG. 2A, immunodetection of PGA in cell surface extracts of the wild-type and complemented strains demonstrated that PGA is synthesized by *S. epidermidis* and attached to the bacterial cell surface. Further, as shown in FIG. 2A, the PGA production level in the complemented strain was 147% of that of the wild-type strain. There was no detectable signal in the cap deletion strain or in any samples obtained from culture filtrates (FIG. 2A).

FIG. 2B includes scanning electron microscopy images of mutant, wild-type, and complemented strains cell surface extracts labeled with immunogold confirming that PGA is located on the *S. epidermidis* cell surface (FIG. 2B). PGA was detected with anti-PGA antiserum.

Next, to verify that the immunoreactive material constituted γDLPGA the immunoreactive material was purified and quantitative and qualitative analyses were performed. In particular, D-glutamic (D-Glu) and L-glutamic (L-Glu) acid levels in *S. epidermidis* PGA were analyzed by stereoselective chromatography and liquid chromatographic-mass spectrometric detection. To determine D- and L-glutamic acid amounts, the L-glutamic acid background detected in the cap mutant strain (Δcap) was subtracted from PGA expression strains.

In contrast to *B. anthracis* PGA, which is entirely composed of D-glutamic acid (Ashiuchi, M., and Misono, H. *Appl. Microbiol. Biotechnol.* 59:9-14, 2002), *S. epidermidis* PGA consisted of about equal amounts of D- and L-glutamic acid (FIG. 2C). Notably, γDLPGA production in *S. epidermidis* was far less than that reported for *B. anthracis* ($1.2\times10^{-6}$ g/l for *S. epidermidis* versus 5-10 g/l for *B. anthracis* (Hariby E. E., and Rydon, H. N. *Biochemistry.* 40: 297-307, 1946). Taken together, the data demonstrate that the cap locus in *S. epidermidis* drives production of a surface-attached form of γDLPGA.

EXAMPLE 4

γPGA Production in *S. Epidermidis* Strains

This example demonstrates that the cap gene locus and PGA production are ubiquitous among *S. epidermidis* strains.

γPGA expression in *S. epidermidis* strains of clinical and commensal origin under low and high salt conditions was determined by immuno-dot blot analysis. First, cells were grown for 24 hours at 37° C. with shaking at 200 rpm. γDLPGA was then purified as described in Example 1, Methods. Results of the present studies are shown in FIG. 3. Horizontal bars in FIG. 3 show the group mean. The membrane background was subtracted from each sample. The studies, including purification and detection, were repeated twice with very similar results.

Some virulence factors in staphylococci, such as PIA, are mostly restricted to invasive strains (Otto, M. *Front. Biosci.* 9: 841-863, 2004; Galdbart, J. O., Allignet, J. Tung, H. S., Ryden, C., and El Solh, N. *J. Infect. Dis.* 182: 351-355, 2000). In contrast, all 74 *S. epidermidis* strains of clinical and commensal origin that were investigated in the present study had the cap gene locus as shown by analytical PCR and were positive for γDLPGA by immuno-dot blot analysis (FIG. 3), indicating that γDLPGA production is ubiquitous in *S. epidermidis*. There was no significant difference in γDLPGA production between commensal and clinical strains (FIG. 3). Therefore, it is believed that γDLPGA is important for the survival of *S. epidermidis* as a skin commensal organism and during infection.

EXAMPLE 5

Role of γDLPGA in Osmoprotection and Inducibility of Cap Expression by NaCl

This example demonstrates that γDLPGA contributes to the ability of *S. epidermidis* to exist in high salt concentrations.

It was determined if γDLPGA impacts survival of *S. epidermidis* under conditions found in its natural habitat, surface of the human skin. The environment on human skin is characterized by high and varying salt concentration. *S. epidermidis* can withstand very high salt concentrations of up to approximately 2 M NaCl, but the reasons for this extraordinary resistance are not completely clear (Otto, M. *Front. Biosci.* 9: 841-863, 2004). Thus, growth (FIG. 4A; $OD_{600}$) and viability (FIG. 4B; CFU) of wild-type and cap mutant strains in Luria-Bertani medium supplemented with 2 M NaCl were evaluated. Bacteria were inoculated from an overnight preculture (1:1,000) and grown in flasks at 37° C. with shaking at 200 rpm. Values presented are the mean±SEM of 3 experiments. *P<0.05; **P<0.01; $^{\#}$P<0.001 (wild-type versus mutant strain).

As shown in FIGS. 4A and 4B, respectively, growth and viability of the cap mutant strain were significantly impaired at high concentrations of NaCl. In contrast, growth at physiological salt concentration was similar for the wild-type and mutant strains.

In addition, NaCl inducibility of cap expression was analyzed by quantitative real-time PCR. Bacteria were grown as described for FIG. 4A with the indicated concentrations of NaCl. Cells were harvested after 6 hours of growth, RNA was isolated, and real-time PCR was performed using a capB probe. Values are the mean±SEM of 3 experiments. Results are presented in FIG. 4C. As shown in FIG. 4C, the relative cap expression increased as the NaCl concentration increased. Similar findings were found with immuno-dot blots. Thus, the present data coupled with findings shown in FIG. 3 (γDLPGA production was greater at high NaCl concentration) suggest that γDLPGA contributes to survival of S. epidermidis on human skin.

EXAMPLE 6

Role of γDLPGA in Immune Evasion and Virulence of S. epidermidis

This example demonstrates that S. epidermidis γDLPGA provides protection from key components of innate host defense.

γDLPGA's contribution to S. epidermidis virulence was investigated. Unlike its more aggressive relative S. aureus, S. epidermidis does not have a large arsenal of virulence factors (Vuong, C., and Otto, M. Microbes Infect. 4:481-489, 2002). Rather, it causes relatively silent, chronic infections during which resistance against attacks by the innate immune system is of special importance to bacterial survival (Vuong, C., and Otto, M. Microbes Infect. 4:481-489, 2002). Therefore, whether cap expression in S. epidermidis affects resistance to key components of innate host defense against bacterial infections, namely antibacterial peptides and neutrophil phagocytosis was investigated.

Resistance to cationic antimicrobial peptides was determined by incubating washed S. epidermidis cells (approximately $10^5$) with LL-37 or human β-defensin 3 in various concentrations of antimicrobial peptides for 2 hours at 37° C. Thereafter, S. epidermidis survivor cells were counted by plating. Results are shown as dose-response curves. The log $LD_{50}$ values for all strain/peptide combinations are given in the key. Statistical analyses are for each peptide concentration. Values of significance were calculated against the wild-type (for Δcap) and Δcap (for capBCAD) strains.

In addition, phagocytosis by human neutrophils was determined after 30 minutes of incubation with S. epidermidis at a ratio of 20 bacteria per PMN.

Figure 5A:
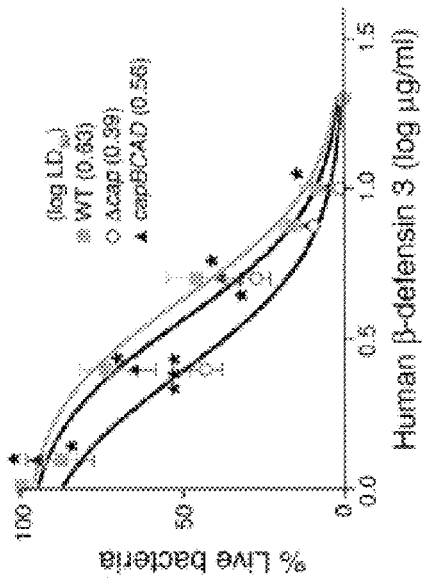
FIGS. 5A and 5B are graphs illustrating the resistance to cationic antimicrobial peptides in wildtype, capBCAD and Δcap following incubation with LL-37 (FIG. 5A) or human β-defensin 3 (FIG. 5B).
Figure 5B:
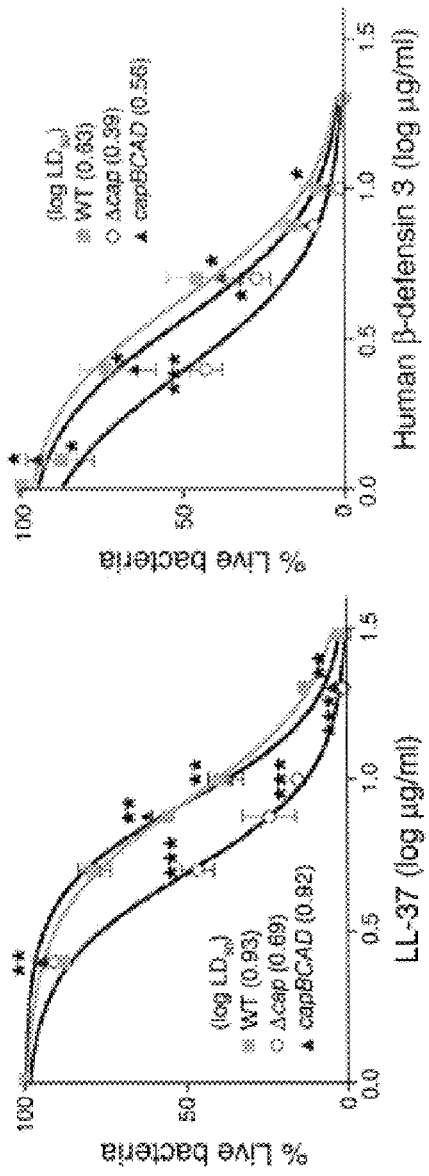
Figure 5C:
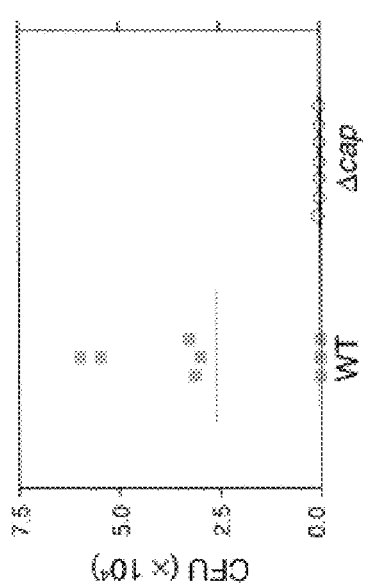
FIG. 5C is a graph depicting the resistance to human neutrophil phagocytosis in wildtype, capBCAD and Δcap following incubation with *S. epidermidis*.

As demonstrated in FIGS. 5A and 5B, the cap mutant strain had significantly reduced resistance to 2 representative antibacterial peptides from human skin and neutrophil specific granules, LL-37 (FIG. 5A) and human β-defensin 3 (FIG. 5B). Further, as shown in FIG. 5C, the cap mutant strain had significantly increased susceptibility to phagocytosis by human neutrophils. For example, the phagocytosis rate was 42% higher with the mutant strain compared to the wild-type strain. This is a relatively large difference compared with what is observed with other single pathogen factors. These findings indicate that γDLPGA plays a critical role in protecting S. epidermidis from the microcidal effects of innate host defense components.

EXAMPLE 7

Role of γDLPGA in Immune Evasion and Virulence of S. epidermidis

This example demonstrates that γDLPGA is indispensable for S. epidermidis persistence on in-dwelling medical devices in an animal infection model.

Figure 5D:
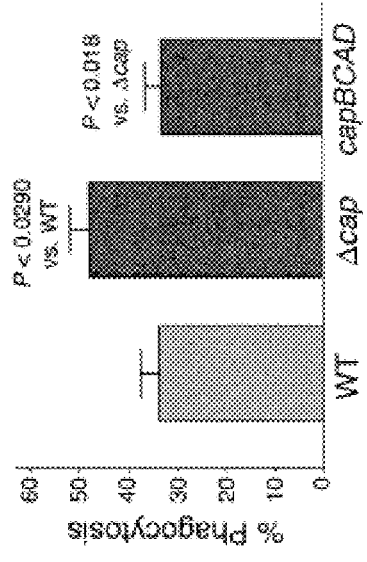
FIG. 5D is a graph demonstrating the viability (CFU) of *S. epidermidis* cells on subcutaneous devices implanted in mice infected with wild type strain of *S. epidermidis* or Δcap mutant strain.

The role of γDLPGA in protection from innate host defense components suggested that γDLPGA facilitates pathogen survival during S. epidermidis infection. Thus, to determine the role of γDLPGA in S. epidermidis persistence, the persistence of wild-type and isogenic cap mutant strains in a mouse model of subcutaneous catheter infection was evaluated. Catheter pieces with equal amounts of adhered S. epidermidis cells ($2 \times 10^5$) were placed under the dorsum of the animals. CFU on implanted devices 1 week after infection were counted. Results are illustrated in FIG. 5D. The horizontal bar shows the group mean. *P<0.05; *P<0.01; *P<0.001.

Importantly, biofilm formation on plastic material and intercellular aggregation in vitro did not differ between wild-type and cap mutant strains, indicating that colonization and persistence in the animal model were not due to differences in the physicochemical interaction with the catheter material. As illustrated in FIG. 5D, most mice (5 of 8) infected with the wild-type strain had significant numbers of bacteria (approximately $3 \times 10^4$-$6 \times 10^4$ CFU) on implanted catheters after 1 week of infection, whereas all 7 mice infected with the cap mutant strain had completely cleared the infection. This pronounced difference indicates that γDLPGA is a key factor for the success of S. epidermidis in device-associated infection, which represents a predominant type of disease caused by this organism. Hence biofilm formation can be inhibited by decreasing expression of γDLPGA from S. epidermidis, by promoting a specific immune response against it, or by otherwise disrupting the formation of γDLPGA by the S. epidermidis.

EXAMPLE 8

Role of γDLPGA in Immune Evasion and Virulence of S. epidermidis

This example demonstrates that a group of coagulase-negative staphylococci related to S. epidermidis also produces γDLPGA.

It is known from publicly available genome sequencing data that the cap locus is absent from S. aureus. To investigate whether other staphylococcal species have the genetic information for γDLPGA production, a series of staphylococcal strains were evaluated for the presence of the cap genes by DNA-DNA hybridization using capB and capD probes and a cocktail of probes from all 4 cap genes. Of 22 strains, representing 16 different species and subspecies, genomic DNA from 11 strains hybridized with probes (Table 1). Except for S. saprophyticus strains, all strains with a signal in the Southern blot also produced surface-attached γDLPGA, which was demonstrated using anti-PGA antisera (Table 1). Although there are some intraspecies differences, it is remarkable that all phylogenetically related members of the S. epidermidis group (S. epidermidis, S. capitis, S. warneri, S. saccharolyticus, S. caprae, S. hominis, and S. haemolyticus) (Saruta, K., et al. FEMS Microbiol. Lett. 146: 271-278, 1997) have the ability to produce γDLPGA, whereas it is far less distributed among other species (Table 1). Therefore, biofilm formation can be inhibited by disrupting γDLPGA in a variety of staphylococci that express γDLPGA. Moreover, Staphylococci can be categorized into those that secrete γDLPGA and those that do not. Secretion positive staphylococci are likely to be in the S. epidermidis group, although there are several exceptions. Hence the antibodies disclosed herein that specifically recognize the γDLPGA and bind to it can be used for diagnostic purposes (for example if they are labeled for detection), for example in the taxonomic classification of such bacteria. Binding of the specific binding agents also indicates that the organisms are candidates for treatment with the methods and compositions disclosed herein.

TABLE 1

PGA production in staphylococci

| Strain | ATCC no. | PGA production[A] | Presence of capB and capD genes[B] |
|---|---|---|---|
| *S. epidermidis* group | | | |
| *S. capitis* subsp. *capitis* | ATCC 27840 | + | + |
| *S. capitis* subsp. *ureolyticus* | ATCC 49324 | + | + |
| *S. caprae* | ATCC 51548 | + | + |
| *S. haemolyticus* | ATCC 29970 | + | + |
| *S. warneri* | ATCC 17917 | + | + |
| *S. warneri* | ATCC 49518 | − | − |
| *S. saccharolyticus* | ATCC 14953 | + | + |
| *S. hominis* subsp. *hominis* | ATCC 25615 | + | + |
| *S. hominis* subsp. *hominis* | ATCC 27844 | − | − |
| Other *staphylococci* | | | |
| *S. schleiferi* subsp. *schleiferi* | ATCC 43808 | − | − |
| *S. pulveri* | ATCC 51698 | − | − |
| *S. simulans* | ATCC 31432 | − | − |
| *S. simulans* | ATCC 700576 | + | + |
| *S. simulans* | ATCC 27848 | − | − |
| *S. xylosus* | ATCC 49148 | − | − |
| *S. xylosus* | ATCC 29966 | − | − |
| *S. saphrophyticus* | ATCC 35552 | − | + |
| *S. saphrophyticus* | ATCC 15305 | − | + |
| *S. cohnii* subsp. *cohnii* | ATCC 29972 | − | − |
| *S. cohnii* subsp. *urealyticum* | ATCC 49328 | − | − |
| *S. lugdunensis* | ATCC 43809 | + | + |
| *S. intermedius* | ATCC 49052 | − | − |
| *S. aureus* | All strains with known genome sequence | ND | − |

[A]By immuno-dot blot analysis.
[B]By Southern blot analysis.
ND, not determined.

EXAMPLE 9

Constructing Immune Conjugates and Linking the Conjugates to a Carrier

Based on the teachings herein, one can construct immune conjugates including *Staphylococcus* capsular γPGA polypeptides (such as γPGA polypeptides). It is contemplated that these immune conjugates can be prepared by isolating and purifying γPGA polypeptides by methods well known in the art. For example, γPGA polypeptides may be isolated and purified by salt fractionation, phenol extraction, precipitation with organic solvents (for example, hexadecyltrimethylammonium bromide (cetavlon) or ethanol), affinity chromatography, ion-exchange chromatography, hydrophobic chromatography, high performance liquid chromatography, gel filtration, isoelectric focusing, and like techniques. Further, it is contemplated that *Staphylococcus* γPGA polypeptide conjugates may include carriers to enhance the immunogenic response. For example, a carrier can be linked to a γDLPGA polypeptide as described in Section III.A.

EXAMPLE 10

Method of Treating an Infection Caused by a *Staphylococcus* Organism that Expresses Cap Genes According to the teachings herein, one can treat an infection caused by a *Staphylococcus* organism that expresses cap genes. In an example, a subject who is at risk or has been diagnosed with the infection by the *Staphylococcus* organism which expresses γPGA, such as γDLPGA, for example from the cap genes is identified. For example, a subject which is to receive or has received an in-dwelling device such as a catheter, artificial joint, pacemaker, and like device is selected for treatment prior to or following laboratory detection of the *Staphylococcus* organism. It is contemplated that the *Staphylococcus* organism can include *S. capitis*, *S. warneri*, *S. saccharolyticus*, *S. caprae*, *S. hominis*, *S. haemolyticus*, *S. lugdunensis*, *S. simulans*, or *S. epidermidis* as well as a combination thereof.

Following subject selection, the expression of γPGA (such as γDLPGA) polypeptide by the organism can be altered. For example, the expression of γPGA can be altered by promoting an immune response against the γPGA. The promoting of the immune response against γPGA can include administering an effective amount of a conjugate. The conjugate can be prepared as described above in Section III.A. In an additional example, promoting the immune response against the γPGA can include interfering with expression of the γPGA such as by inhibiting expression of the γDLPGA by the cap genes. In a further example, promoting the immune response against the γPGA entails administering an effective amount an antiserum. The antiserum includes an effective amount of anti-γPGA antibodies effective to enhance an immune response against the organism. The anti-γPGA antibodies can be prepared by skills well known in the art as well as by methods described previously in Section III.B. In another example, the expression of γPGA is inhibited and thereby formation of a biofilm associated with the organism is inhibited or rendered more susceptible to immunosurvilleance and elimination. Further, a subject can be given an antisera or siRNA that disrupts formation or maintenance of the γPGA (such as γDLPGA), thus rendering the biofilm susceptible to immune response.

While this disclosure has been described with an emphasis upon preferred embodiments, it will be obvious to those of ordinary skill in the art that variations of the preferred embodiments may be used and it is intended that the disclosure may be practiced otherwise than as specifically described herein. Accordingly, this disclosure includes all modifications encompassed within the spirit and scope of the disclosure as defined by the claims below.

We claim:

1. A method of detecting an organism from a *Staphylococcus epidermidis* group in a subject, comprising:
   detecting the presence of poly-γ-DL-glutamic acid (γDLPGA) in a *Staphylococcus* obtained from the subject, wherein presence of γDLPGA indicates the organism is a member of the *Staphylococcus epidermidis* group.

2. The method of claim 1, wherein the members of the *Staphylococcus epidermidis* group comprises: *S. capitis, S. warneri, S. saccharolyticus, S. caprae, S. hominis*, and *S. haemolyticus*.

3. The method of claim 2, wherein the subject is at risk of or has been diagnosed with an infection by the *Staphylococcus*.

4. The method of claim 2, wherein the subject has an in-dwelling medical device.

* * * * *

SEQUENCE LISTING

```
<160> NUMBER OF SEQ ID NOS: 21

<210> SEQ ID NO 1
<211> LENGTH: 26
<212> TYPE: DNA
<213> ORGANISM: Artificial sequence
<220> FEATURE:
<223> OTHER INFORMATION: capF seqencing primer
```

```
<400> SEQUENCE: 1
catgaagctg agaatgcact tgtatt                                          26

<210> SEQ ID NO 2
<211> LENGTH: 16
<212> TYPE: DNA
<213> ORGANISM: Artificial Sequence
<220> FEATURE:
<223> OTHER INFORMATION: CapProbe sequencing primer

<400> SEQUENCE: 2
aacatccacg gcccgg                                                     16

<210> SEQ ID NO 3
<211> LENGTH: 26
<212> TYPE: DNA
<213> ORGANISM: Artificial sequence
<220> FEATURE:
<223> OTHER INFORMATION: capR sequencing primer

<400> SEQUENCE: 3
ctatcccttc tatgaattcc gctatt                                          26

<210> SEQ ID NO 4
<211> LENGTH: 40
<212> TYPE: DNA
<213> ORGANISM: Artificial Sequence
<220> FEATURE:
<223> OTHER INFORMATION: CapEco oligonucleotide used for allelic
      replacement of the cap locus

<400> SEQUENCE: 4
ccaccaatat ccgttgcttg aggtgcagca gaattcatcc                           40

<210> SEQ ID NO 5
<211> LENGTH: 41
<212> TYPE: DNA
<213> ORGANISM: Artificial sequence
<220> FEATURE:
<223> OTHER INFORMATION: CapBam oligonucleotide used for allelic
      replacement of the cap locus

<400> SEQUENCE: 5
gggtattggt acaccaggtg ggaacaagga tccaacaatt c                         41

<210> SEQ ID NO 6
<211> LENGTH: 43
<212> TYPE: DNA
<213> ORGANISM: Artificial sequence
<220> FEATURE:
<223> OTHER INFORMATION: CapSal oligonucleotide used for allelic
      replacement of the cap locus

<400> SEQUENCE: 6
gcgcaacaca cgctataatg agtaacagtc gactttacct ctc                       43

<210> SEQ ID NO 7
<211> LENGTH: 43
<212> TYPE: DNA
<213> ORGANISM: Artificial sequence
<220> FEATURE:
<223> OTHER INFORMATION: CapHind oligonucleotide used for allelic
      replacement of the cap locus

<400> SEQUENCE: 7
catgtcttta ccatttaagc ttccaataag tataaatgcg agg                       43
```

```
<210> SEQ ID NO 8
<211> LENGTH: 43
<212> TYPE: DNA
<213> ORGANISM: Artificial sequence
<220> FEATURE:
<223> OTHER INFORMATION: capBam2 oligonucleotide used for construction
      of complementation vectors

<400> SEQUENCE: 8
caatcatcat actacttctt tcattcattg gatccgctta cac                     43

<210> SEQ ID NO 9
<211> LENGTH: 37
<212> TYPE: DNA
<213> ORGANISM: Artificial sequence
<220> FEATURE:
<223> OTHER INFORMATION: capXba oligonucleotide used for construction
      of complementation vectors

<400> SEQUENCE: 9
gacttctcca tacctctcct cctctagacg taatatc                            37

<210> SEQ ID NO 10
<211> LENGTH: 41
<212> TYPE: DNA
<213> ORGANISM: Artificial sequence
<220> FEATURE:
<223> OTHER INFORMATION: CAP1 oligonucleotide used to confirm lack of
      cap expression in the cap mutant strain by real time PCR

<400> SEQUENCE: 10
cccttctatg aattccgcta ttctaccacc ccgggccgtg g                       41

<210> SEQ ID NO 11
<211> LENGTH: 34
<212> TYPE: DNA
<213> ORGANISM: Artificial sequence
<220> FEATURE:
<223> OTHER INFORMATION: CAP2 oligonucleotide used to confirm lack of
      cap expression in the cap mutant strain by real time PCR

<400> SEQUENCE: 11
gacgtcatac cagaatcata tttacggaag ttcg                               34

<210> SEQ ID NO 12
<211> LENGTH: 20
<212> TYPE: DNA
<213> ORGANISM: Artificial sequence
<220> FEATURE:
<223> OTHER INFORMATION: C2P1 oligonucleotide used to confirm lack of
      cap expression in the cap mutant strain by real time PCR

<400> SEQUENCE: 12
gatattgatc acaactcacc                                               20

<210> SEQ ID NO 13
<211> LENGTH: 20
<212> TYPE: DNA
<213> ORGANISM: Artificial sequence
<220> FEATURE:
<223> OTHER INFORMATION: C2P5 oligonucleotide used to confirm lack of
      cap expression in the cap mutant strain by real time PCR

<400> SEQUENCE: 13
gccattatct gtgttttcac                                               20
```

<210> SEQ ID NO 14
<211> LENGTH: 40
<212> TYPE: DNA
<213> ORGANISM: Artificial sequence
<220> FEATURE:
<223> OTHER INFORMATION: CapSB2 oligonucleotide used for amplification
      of the capB probe (Southern blot)

<400> SEQUENCE: 14
atgtgatgga agaccatatg gatgtcttag gaccgacact                    40

<210> SEQ ID NO 15
<211> LENGTH: 40
<212> TYPE: DNA
<213> ORGANISM: Artificial Sequence
<220> FEATURE:
<223> OTHER INFORMATION: CapSB3 oligonucleotide used for amplification
      of the capB probe (Southern blot)

<400> SEQUENCE: 15
cgcttttgta gactgcggtt cattagcagc gaatgcatta                    40

<210> SEQ ID NO 16
<211> LENGTH: 40
<212> TYPE: DNA
<213> ORGANISM: Artificial sequence
<220> FEATURE:
<223> OTHER INFORMATION: CapSB-D3 oligonucleotide used for amplification
      of the capB probe (Southern blot)

<400> SEQUENCE: 16
atccttgaag cattaatgtg cctcctaaag gattaggtgc                    40

<210> SEQ ID NO 17
<211> LENGTH: 40
<212> TYPE: DNA
<213> ORGANISM: Artificial sequence
<220> FEATURE:
<223> OTHER INFORMATION: CapSB-D4 oligonucleotide used for amplification
      of the capB probe (Southern blot)

<400> SEQUENCE: 17
ctcattcatc aggactagga ggtggcggtg cgacacttac                    40

<210> SEQ ID NO 18
<211> LENGTH: 40
<212> TYPE: DNA
<213> ORGANISM: Artificial sequence
<220> FEATURE:
<223> OTHER INFORMATION: CapSB-A1 oligonucleotide used for amplification
      of the capB probe (Southern blot)

<400> SEQUENCE: 18
aatgacatct gcaccagcat tcgctaacgc atgtgcatat                    40

<210> SEQ ID NO 19
<211> LENGTH: 40
<212> TYPE: DNA
<213> ORGANISM: Artificial sequence
<220> FEATURE:
<223> OTHER INFORMATION: CapSB-A2 oligonucleotide used for amplification
      of the capB probe (Southern blot)

<400> SEQUENCE: 19
gagagacaaa gatagcattc gtatcaccta tttaggtaac                    40

<210> SEQ ID NO 20
<211> LENGTH: 42

```
<212> TYPE: DNA
<213> ORGANISM: Artificial sequence
<220> FEATURE:
<223> OTHER INFORMATION: CapSB-C1 oligonucleotide used for amplification
      of the capB probe (Southern blot)

<400> SEQUENCE: 20
gacaacacct atacctgaaa cttcaaccat ttcaaatggg tc                          42

<210> SEQ ID NO 21
<211> LENGTH: 40
<212> TYPE: DNA
<213> ORGANISM: Artificial sequence
<220> FEATURE:
<223> OTHER INFORMATION: CapSB-C2 oligonucleotide used for amplification
      of the capB probe (Southern blot)

<400> SEQUENCE: 21
gctgagaaat ttgggattaa tccagcaggg ttagtcgttc                             40
```